United States Patent [19]
Chum et al.

[11] Patent Number: 5,235,021
[45] Date of Patent: Aug. 10, 1993

[54] RESOLE RESIN PRODUCTS DERIVED FROM FRACTIONATED ORGANIC AND AQUEOUS CONDENSATES MADE BY FAST-PYROLYSIS OF BIOMASS MATERIALS

[76] Inventors: Helena L. Chum, 8448 Allison Ct., Arvada, Colo. 80005; Stuart K. Black, 4976 Raleigh St., Denver, Colo. 80212; James P. Diebold, 57 N. Yank Way, Lakewood, Colo. 80228; Roland E. Kreibich, 4201 S. 344th, Auburn, Wash. 98001

[21] Appl. No.: 806,897

[22] Filed: Dec. 16, 1991

Related U.S. Application Data

[63] Continuation-in-part of Ser. No. 456,653, Dec. 29, 1989, Pat. No. 5,091,499.

[51] Int. Cl.$^5$ .................... C08G 8/04; B66C 1/00; B32B 21/08; C08J 11/00
[52] U.S. Cl. .................... 528/129; 294/66.1; 428/529; 524/16; 568/762
[58] Field of Search .................... 528/129; 294/66.1; 428/529; 524/16; 568/762

[56] References Cited

U.S. PATENT DOCUMENTS

| | | | |
|---|---|---|---|
| 3,293,200 | 12/1966 | MacGregor et al. | 568/762 |
| 4,209,647 | 6/1980 | Gallivan et al. | 568/762 |
| 4,508,886 | 4/1985 | Russell et al. | 568/762 |

*Primary Examiner*—John Kight, III
*Assistant Examiner*—T. Mosley
*Attorney, Agent, or Firm*—Antonelli, Terry, Stout & Kraus

[57] ABSTRACT

A process for preparing phenol-formaldehyde resole resins by fractionating organic and aqueous condensates made by fast-pyrolysis of biomass materials while using a carrier gas to move feed into a reactor to produce phenolic-containing/neutrals in which portions of the phenol normally contained in said resins are replaced by a phenolic/neutral fractions extract obtained by fractionation.

94 Claims, 8 Drawing Sheets

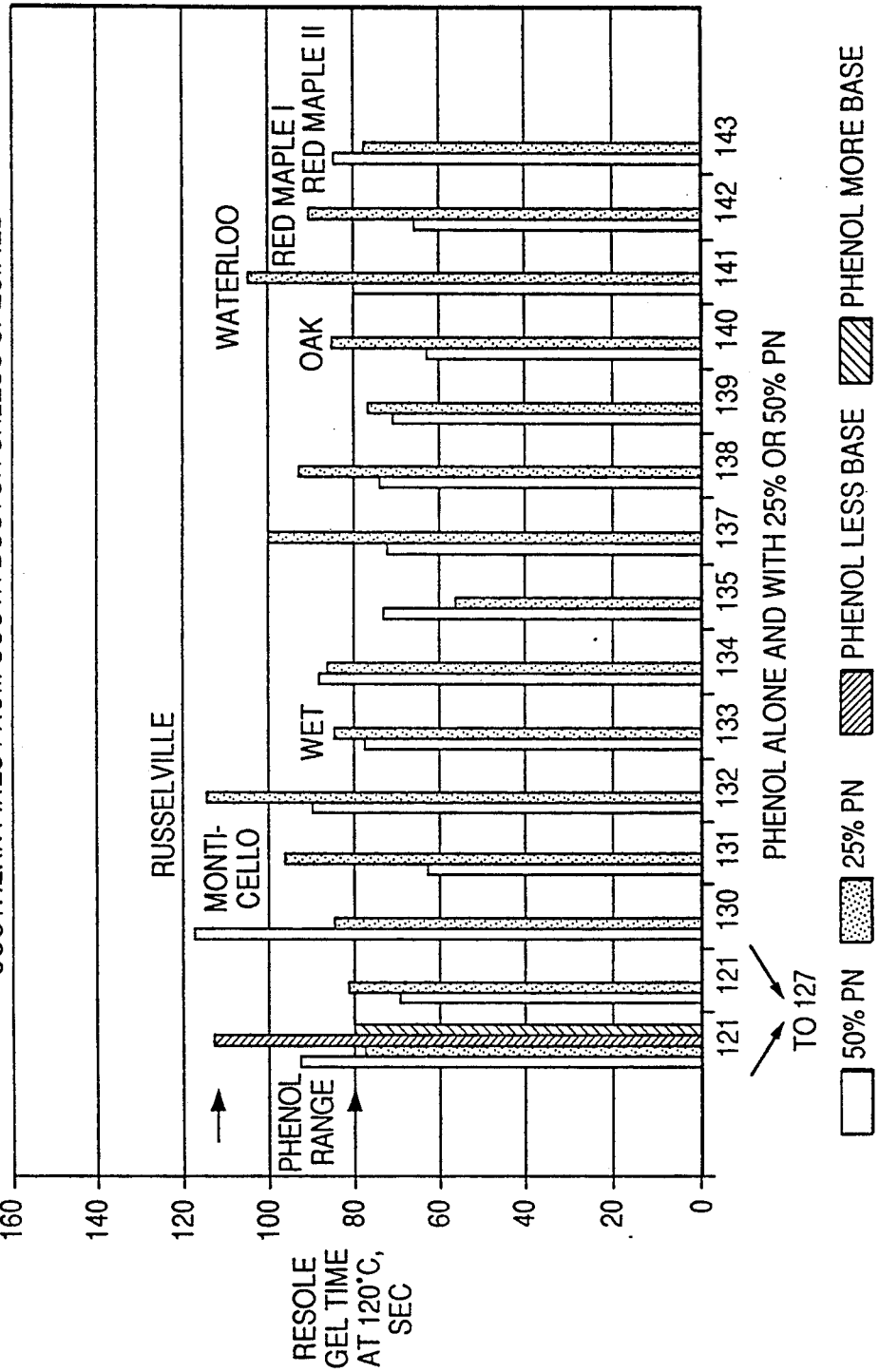

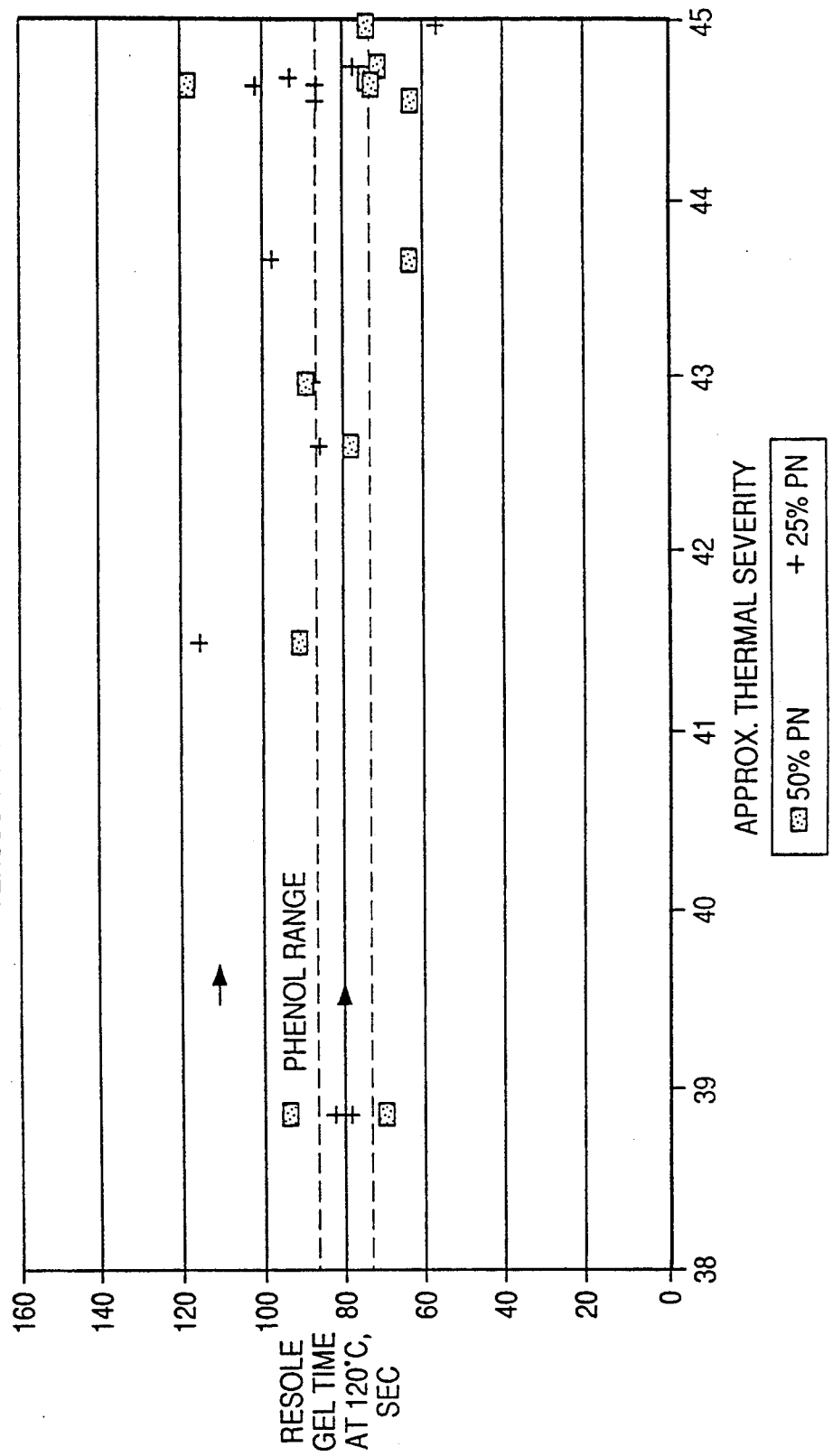

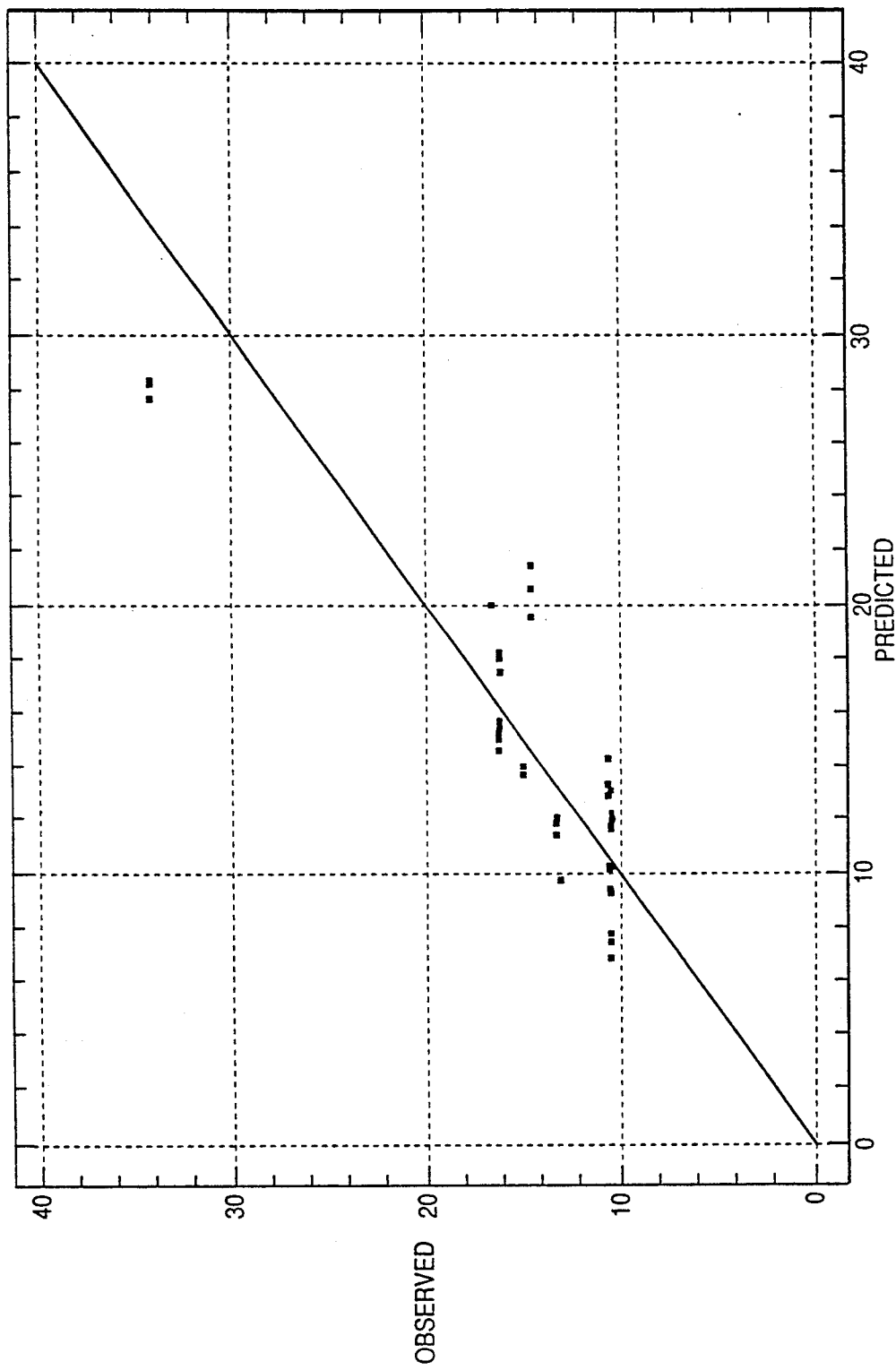

RESOLE RESIN PRODUCTS DERIVED FROM FRACTIONATED ORGANIC AND AQUEOUS CONDENSATES MADE BY FAST-PYROLYSIS OF BIOMASS MATERIALS

CONTRACTUAL ORIGIN OF THE INVENTION

The United States Government has rights in this invention under Contract No. DE-AC02-83CH10093 between the United States Department of Energy and the Solar Energy Research Institute, a Division of the Midwest Research Institute.

BACKGROUND OF THE INVENTION

1. Field of the Invention

The present invention is a Continuation-in-part application of original U.S. application Ser. No. 07/456,653 now U.S. Pat. No. 5,091,499 filed Dec. 29, 1989, and the present application incorporates Ser. No. 07/456,654 now U.S. Pat. No. 5,091,499 by reference in its entirety. The invention relates to the production of phenolic type resole resins from biomass materials and, more particularly, to the treatment of fast-pyrolysis oils derived from lignocellulosic materials to make phenolic type resole resins. Specifically, the present invention relates to taking phenolics/neutrals fractions (P/N) and rendering them suitable for the production of phenolic type resole resins, subsequent to obtaining said fractions from fast-pyrolysis oils derived from lignocellulosic materials.

2. Description of the Prior Art

Adhesive resins such as resoles are utilized in a wide variety of applications, inclusive of which is the bonding of wood layers to manufacture plywood, and a variety of composite boards. However, certain disadvantages are attendant to existing techniques for manufacturing these different types of phenolic resins.

For example, phenol has been traditionally derived from petroleum-based products; however, the production of petroleum-based phenol is quite expensive, and efforts in the industry in recent years have been to at least partially substitute the phenol in such resins with inexpensive phenols derived from wood-based products or extracts. More specifically, phenols derived from bark, wood chips and the like have been looked at as a potential substitute for petroleum-based phenol in such resins.

The pyrolysis of biomass, and in particular lignocellulosic materials, is known to produce a complex mixture of phenolic compounds. In nature, lignin acts as an adhesive to bind the cellulose fibers together. Therefore, lignin and lignin-derived material from wood would appear to be a natural starting point for the development of biomass-based adhesive resins. Sources for such phenolic materials include black liquor from kraft pulping and other pulping processes, where the lignin is present in a stream which is commonly burned to recover process heat and chemicals.

Unfortunately, these lignins are generally not very reactive after recovery for a variety of reasons, such as high molecular weight, chemical modification during recovery due to condensation reactions and the like, and lack of reproducibility of properties. Various types of pyrolysis processes have also been utilized, frequently yielding similar kinds of results; however, fast-pyrolysis, which proceeds at temperatures between about 450° C. to about 600° C. and has short vapor residence times in the order of seconds has not been used.

Fast-pyrolysis of biomass features the depolymerization of cellulosic, lignin, and hemicellulosic polymers which produces an oil having a relatively low molecular weight and which has considerable chemical activity under proper conditions. Crude pyrolysis oil apparently undergoes a limited amount of repolymerization due to condensation. However, the thermal stability of fast-pyrolysis oils at room temperature is qualitatively quite good imparting a good shelf life for the oils, although at 100° C. the crude oils solidify overnight. Solidified pyrolysis oils are characterized by their low strength and brittleness. The potential of pyrolysis products for use in adhesive resins is not a new concept, as indicated above, but the efficient and cost-effective reduction of this approach to practice has been an elusive goal over many years.

The general approach of producing phenols from biomass has previously been to purify the phenolic fractions present in the pyrolysis oils by the use of solvents to partition the constituents by differences in solubility and reactivity. Different variations of solvents, reagents, and sequence of extractions have been developed in the past, and this has resulted in different partitioning coefficients for a couple of hundreds of chemical compounds known to be in pyrolysis oils, and therefore produced extracts having differing relative compositions. Another significant difference between various research efforts pertaining to this area in the past has been the type of pyrolysis process used to produce the oils used as feed in the extraction process. These include updraft gasification, entrained fast-pyrolysis, and fluidized bed fast-pyrolysis, all at atmospheric pressures, as well as slow, high pressure liquefaction processes. In addition, both hardwoods and softwoods have been used as feedstock in the past for the oil forming processes. These differences in extraction and pyrolysis processes, coupled with the differences in feedstock, yield different materials as products. Thus, the usefulness of a particular extract as an adhesive component is quite different, one from the other.

U.S. Pat. Nos. 4,209,647 and 4,223,465 disclose methods for recovering phenolic fractions from oil obtained from pyrolysis of lignocellulosic materials and the subsequent use of that fraction in making of phenol-formaldehyde resins. However, these processes use pyrolysis oils which are usually formed at ill-defined temperatures and which have undergone phase separation cracking and some condensation, and suffer from very low yields.

A number of other patents including U.S. Pat. Nos. 2,172,415, 2,203,217, 3,069,354, 3,309,356 and 4,508,886 as well as Japanese Patent No. 38-16895 all disclose a variety of processes for recovering phenolic fractions from oils derived from biomass materials and derived resources such as wastes. These processes vary in the particular procedures and techniques utilized to ultimately separate the phenolic fractions as well as the procedures utilized to derive the oil from the biomass or other feed material. However, they all have a common thread linking them in that the ultimate end product is a phenolic fraction, which is desired to be as pure as possible. This phenolic fraction is then utilized to produce phenol-formaldehyde thermosetting resins. The phenol substitutes usually were slower than phenol derived from petroleum-based products. The complex procedures disclosed in these references to produce relatively pure phenolic fractions are not particularly economical. Thus, there is still a need for a process designed to produce pyrolysis oils from lignocellulosic materials and then extract a phenolic composition from such oils which is capable of functioning as efficiently as petroleum-based phenols in the formation of phenol-formaldehyde resins and which is less expensive to produce.

SUMMARY OF THE INVENTION

Accordingly, it is one object of the present invention to provide phenolic type resole resins, in which the phenol content is in part replaced by a phenolic-compounds-containing/neutral fractions (P/N) from fast pyrolysis oils derived from lignocellulosic materials.

Another object of the present invention is to provide inexpensive adhesive compositions comprising phenolic type resole resins, in which the phenol content is in part replaced by a P/N fraction from fast-pyrolysis oils derived from lignocellulosic materials.

Another object of the present invention is to provide phenolic compounds-containing/neutral fractions extract, wherein the neutral fractions have molecular weights of from 100–800.

The foregoing and other objects in accordance with the present invention, as embodied and broadly described herein, is accomplished by: admixing said oils with an organic solvent having a solubility parameter of approximately 8.4–9.1 $[cal/cm^3]^{\frac{1}{2}}$ polar components in the 1.8–3.0 range and hydrogen bonding components in the 2–4.8 range; separating the organic solvent-soluble fraction containing the phenolic compounds-containing/neutral fractions from said mixture and admixing it with water to extract water-soluble materials therefrom; separating the organic solvent-soluble fraction from said water fraction and admixing said solvent fraction with an aqueous alkali metal bicarbonate solution to extract strong organic acids and highly polar compounds from said solvent fractions; and separating the residual organic solvent soluble fraction and removing the organic solvent therefrom to produce said phenolic compounds/neutral fractions extract.

The objects in accordance with the present invention, as embodied and broadly described herein, can further be accomplished by: admixing said oils which contains organic and aqueous condensates with basic materials in a relatively dry, solid state and selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, hydrates thereof, or mixtures thereof, and chosen to be able to neutralize acidic components of the condensates and to render such acidic components and other polar compounds less soluble in the organic phase; admixing said neutralized condensates with an organic solvent having at least a moderate solubility parameter and good hydrogen bonding capability, said organic solvent has a solubility parameter of approximately 8.4 to 9.1 $(cal/cm^3)^{\frac{1}{2}}$ with polar components in the 1.9–3.0 range and hydrogen bonding components in the 2–4.5 range, utilizing said solvent to extract phenolic-containing and neutral fractions from the organic aqueous phases into the solvent phase; separating the organic solvent-soluble fraction having the phenolic-compounds-containing and neutral fractions from the aqueous fraction; and removing the organic solvent therefrom to produce said phenolic-compounds-containing and neutrals compositions in a form substantially free from said solvent.

BRIEF DESCRIPTION OF THE DRAWINGS

The accompanying drawings which are incorporated in and form a part of the specification illustrate preferred embodiments of the present invention, and together with the description, serve to explain the principals of the invention. In the drawings:

FIG. 5 is a graph of gel times for resoles.

FIG. 6 is a graph of gel times for resoles versus thermal treatment severity.

FIG. 7 is a graph showing comparison of gel times for resoles verses thermal treatment severity.

FIG. 8A is a graph of thermal severity for phenol resole extractables, where the FTIR spectrum for samples F4 (1711 $cm^{-1}$), F3 (1263 $cm^{-1}$) and F2 (1557 $cm^{-1}$) and F1 (1109 $cm^{-1}$), all at pH 4, for predicted and observed values.

DETAILED DESCRIPTION OF THE PREFERRED EMBODIMENT

Figure 1:
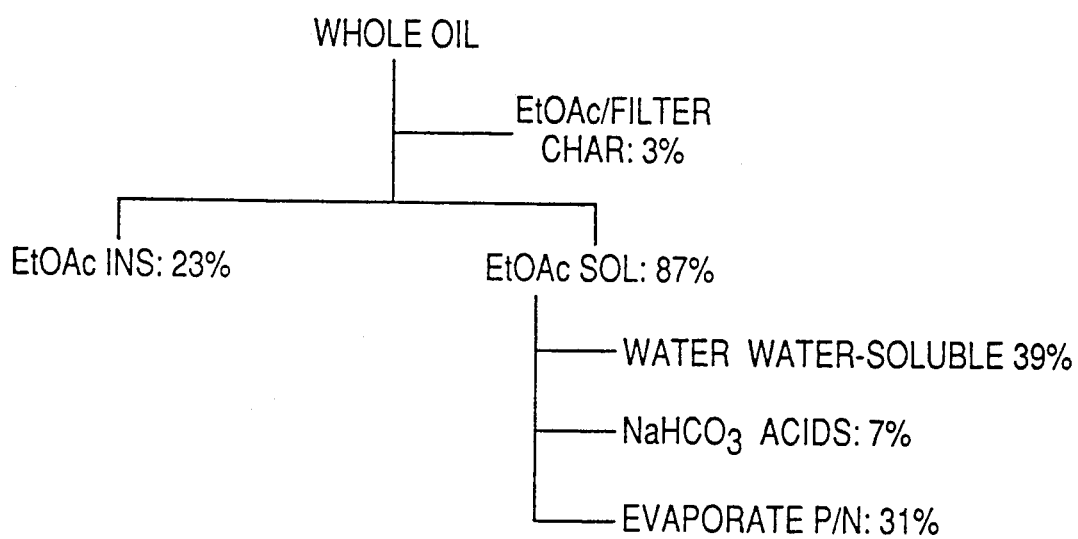
FIG. 1 is a flow diagram that shows evaporate P/N at 33%.

During the course of studying the problem of producing inexpensive but effective phenolic compositions from biomass, it was discovered that certain polar organic solvent having at least a moderate solubility parameter, moderate degree of polarity, and good hydrogen bonding capabilities were capable of extracting both phenolic compounds and neutral fractions from fast-pyrolysis oils. Moreover, it was discovered that this extraction technique was equally effective for fast-pyrolysis oils of differing starting materials. Thus, it was discovered that the present invention may be utilized with pyrolysis oils derived from redwood, pine sawdust, bark, grasses, softwoods as well as certain hardwoods with very little differences in the final results. Apparently, the fast-pyrolysis process preserves the delicate products in monomeric and oligomeric states. A key factor in the process of the present invention is that the oils derived from the lignocellulosic materials must be done so utilizing a fast-pyrolysis. Fast-pyrolysis is generally known in the art, and such a technique has been specifically disclosed in an article entitled, "Production of Primary Pyrolysis Oils in a Vortex Reaction", American Chemical Society Division of Fuel Chemistry Preprints, Vol. 32, No. 2, pp. 21–28 (1987). Thus, details of such fast-pyrolysis techniques need not be specifically repeated and disclosed herein, and the contents of this Article are therefore specifically incorporated herein by reference. Oils from other fast-pyrolysis concepts are also good feedstocks. Such concepts are referenced in "Fast-Pyrolysis of Pretreated Wood and Cellulose", Ibidem, pp. 29–35 (1987), and "Preliminary Data for Scale up of a Biomass Vacuum Pyrolysis Reactor", Ibidem, pp. 12–20 (1987); "The Role of Temperature in the Fast-Pyrolysis of Cellulose and Wood", "Industrial Engineering Chemistry Research", Vol. 27, pp. 8–15 (1988), and "Oil From Biomass by Entrained flow Pyrolysis", Biotechnology and Bioengineering Symposium, No. 14, pp. 15–20 (1984).

In general, in such fast-pyrolysis the particulate biomass solids enter tangentially at high velocities into a vortex reactor tube which has an internal surface design that guides the centrifuged solids into a tight helical pathway on the reactor wall. This results in a very high heat transfer to the wood or other feedstock particles which allows mild cleavage of the polymeric components of the feedstock. Consequently, high yields (greater than 55%) of dry woods and bark oils are generally obtained. If the feedstock is not fully pyrolyzed, the solids enter a recycle loop located at the end of the vortex reactor. After attrition to a powder, char particles elute with the vapor stream and are isolated in a char cyclone. The P/N samples numbers 1–30 were produced using this concept of fast pyrolysis with steam or nitrogen as carrier gas for the process.

Alternative methods to produce primary pyrolysis oils thought to be similar to fast-pyrolysis include fast-pyrolysis in fluidized beds and in entrained flow reactors.

One example utilizing a fluidized bed reactor to produce a P/N material is sample #31, as shown in Table III. A fluidized bed was operated at 2.4 kg/h and was heated by hot gases. P/N sample #31 was produced with a South Boston Southern pine feed, under conditions similar to those of samples #17 and #20, and the reactor was operated by circulating recycled gases instead of the steam used in the fast pyrolysis reactor.

Examples utilizing oils from an entrained flow reactor are P/N samples #32 and #33, as shown in Table III. An entrained flow reactor operating at 30 kg/h was heated using sand as the heat transfer medium to generate two samples from Maple I and II, which were produced using different residence times in the reactor. These samples were prepared in the low thermal severity range, as these ranges are known to be employed for the production of flavor compounds that provide commercially useful flavor extracts. In this pyrolyzer, recycled gases from pyrolysis are also used instead of steam as carrier gases.

Utilizing the process of the present invention, the pyrolysis oils are fractionated in a unique way which produces a combined phenolics and neutral fraction of high phenolic hydroxyl and aldehyde content. In general, a polar organic solvent is added to the oils to separate the phenol and neutral fractions from said oils. The organic solvent-soluble fraction is then admixed with water to extract water-soluble materials, and then further washed with an aqueous alkali metal bicarbonate solution to extract strong organic acids and highly polar compounds. The residual organic solvent-soluble fraction containing the phenol and neutral fractions is then isolated, and the organic solvent is removed, preferably by evaporation, to produce a phenolic compounds-containing composition having most of the phenolics and neutral fractions of the original raw oils. The yield of the phenolics and neutrals fraction in the extract is about 30% of the fast-pyrolysis oil derived from sawdust and about 50% of the oil derived from bark.

In prior art phenol-producing processes, the processes ended only after the phenolic-containing compositions were generally reduced to purified phenolics only, with the neutral fractions also being removed. By neutral fractions, it is meant those compounds which are not solubilized by a strong base such as sodium hydroxide, and have molecular weights of approximately 100–800. Such neutral fractions include carbonyl compounds, furfural-type compounds and the like. It was apparently previously believed that such neutral fractions must also be extracted in order to provide a phenolics composition which may be utilized as a substitute for petroleum based phenol in the production of phenol-formaldehyde adhesive resins. It has been discovered, however, that by utilizing the process of the present invention, the resultant composition containing both phenolics and neutral fractions function just as well as and in some aspects better than a relatively pure phenol composition in the production of phenol-formaldehyde resins because, since the compositions have aldehyde groups, much less formaldehyde is needed to make these formulations. Reduced formaldehyde levels lead to minimization of potential environmental problems. In addition, the economics are such that, it is substantially less expensive to manufacture the combined phenolics and neutral fraction composition. Moreover, by utilizing the entire fraction which includes phenolic compounds and neutral compounds as feedstocks for resins, it was found that this prevented the pyrolysis-derived reactive phenolics from undergoing air oxidation under alkaline conditions, which is what prevails when one isolates and purifies the phenolics fraction alone. This latter air oxidation which can be a problem is a type of condition that prevails in many prior art techniques and is accomplished by extractions with aqueous sodium hydroxide solutions, and accompanied by the formation of insoluble tars and reduced yields of phenolics.

Investigations of the fractionation scheme of the present invention as generally described above utilizing pine fast-pyrolysis oils were carried out employing a number of different solvents to determine the preferred and optimum solvents and the requirements thereof. In general, the whole oil was first dissolved in the organic solvent preferably in an oil:solvent ratio of 0.5:1 to 1:3 by weight. The oil was initially filtered to separate char which is carried over from the pyrolysis reactor operations. Upon standing, the solvent/oil mixture then separates into two phases, the solvent-soluble phase and the solvent-insoluble phase.

One requirement for the organic solvent is that the solvent and water exhibit low mutual solubility. Preferably, acceptable solvents include those with solubilities that are not more than about 10 grams of solvent in 100 grams of water and about 3 grams of water in 100 grams solvent, in terms of mutual solubility. Thus, this solvent requirement eliminates all low-molecular-weight alcohols (methanol, ethanol, propanol) that are infinitely soluble in water, methylethylketone, the carboxylic acids (formic, acetic and propionic) which are infinitely soluble in water, and methyl formate. The classes of solvents that would be acceptable only from a pure mutual solubility point of view include hydrocarbons (aliphatic, aromatic), higher alcohols (greater than 6 carbon atoms), higher ketones (greater than 5 carbon atoms), esters (greater than 2 carbon atoms), ethers, polychlorinated hydrocarbons, and higher nitriles (greater than 4 carbon atoms).

Another requirement for the organic solvent which further limits potential candidates is that the solvent must have a low boiling point or a low-boiling point solvents are the isomers of those listed in Table 1. Mixtures of esters are also acceptable as are mixtures of the higher ketones. Ternary solvent systems also are possible, primarily mixtures of esters and high molecular weight esters such as diisopropylether to reduce the boiling point. However, the most preferred solvents for use with the present invention are ethyl acetate, as indicated above, as well as butyl acetate and methylisobutylketone.

TABLE I

| Property | Acetate Esters | | | Methyl Ketones | | | Ethyl Ketone |
|---|---|---|---|---|---|---|---|
| | Ethyl | Propyl | Butyl | i-Butyl | i-Amyl | i-Propyl | Ethyl |
| Mol. Wt | 88.1 | 102.1 | 116.2 | 100.2 | 114.2 | 86.14 | 86.14 |
| Boiling Point, °C. (at 760 mmHg) | 77.1 | 101.5 | 126.1 | 116.5 | 144 | 92 | 102.0 |
| Density, @ 20° C. | 0.90 | 0.89 | 0.88 | 0.80 | 0.88 | 0.81 | 0.81 |
| Heat Vaporization, | | | | | | | |
| kcal/mole (20° C.) | 8.4 | 9.3 | 10.4 | 10.00 | | | |
| kcal/mole (b.p.) | 7.71 | 8.20 | 8.58 | 8.50 | | 7.73 | 8.06 |
| Solubility, wt % in water | 8.08 | 2.3 | 0.43 | 1.7 | ~0 | ~2 | 2.4 |
| Water in Azeotrope | 2.94 | 3.9 | 1.86 | 1.9 | ~0 | ~2 | 2.6 |
| Water wt % | 9.47 | 14 | 28.7 | 24.3 | 44.0 | | 24 |
| boiling point, °C. | 70.38 | 82.2 | 90.2 | 87.9 | 94.7 | | 82.9 |
| Dielectric | 6.02 | 6.00 | 5.01 | 13.11 | | | 17.0 |
| Solubility param. Total | 9.1 | 8.4 | 8.46 | 8.57 | 8.55 | 8.5 | 8.8 |
| Dispersive comp. | 7.44 | 6.6 | 7.67 | 7.49 | 7.80 | | ~7.8 |
| Polar comp. | 2.6 | 2.0 | 1.8 | 3.0 | 2.8 | | ~3.4 |
| H-Bonding comp. | 4.5 | 4.8 | 3.1 | 2.0 | 2.0 | | 2.0 | azeotrope. The preferred boiling point is around 100° C., although this is somewhat relative. Yet another requirement for the organic solvent is that the solvent have some degree of polarity, preferably high polarity, as well as high hydrogen bonding capability in addition to a moderate-to-good solubility parameter. The solubility parameter is defined as a measure of all the intermolecular forces present in the solvent. The overall solubility parameter is composed of components due to dispersive forces, polar forces (caused by a high dipole moment in the molecule), and hydrogen bonding capability. These three-component Hansen parameters are determined in accordance with an article commencing on page 141 of the "CRC Handbook of Solubility Parameters and Other Cohesion Parameters" by Allan F. M. Barton, 1983. Solubility parameters, measures in $[cal/cm^3]^{\frac{1}{2}}$, range from 5-7 for hydrocarbons and nonpolar solvents, to 14.5 for methanol and 23.4 for water-highly polar substances. Thus, low boiling point ethers, such as diethyl ether, are excluded from being preferred solvents since they have very low solubility parameters (7.4) and very low polar components (1.4). Hydrocarbons are also excluded as preferred solvents because of their very low polar components and overall low solubility parameters.

It has been found that the preferred group of solvents for use in the present invention include acetate and propionate esters, methyl alkyl ketones and ethyl alkyl ketones. More specific preferred organic solvents are listed below in Table I, the most preferred being ethyl acetate due to its availability, relatively low solubility in water, and high oil solubility. The most preferred range for solubility parameters includes 8.4-9.1 with polar components in the 1.8-3.0 range and hydrogen bonding components in the 2.4-5 range. Additional acceptable As indicated above, the preferred solvent is ethyl acetate, and the process of the present invention will hereinafter be described in terms of utilizing ethyl acetate as the solvent. However, it should be understood that any of the identified solvents may be utilized in the following described process. As previously indicated the whole oil is dissolved in the ethyl acetate at a preferred pH of about 2-4 and then filtered. Upon standing, the ethyl acetate/pyrolysis oils mixture separates into two phases. Chemical spectroscopic analysis revealed that the ethyl acetate-insoluble fraction contains carbohydrate and carbohydrate-derived products. The ethyl acetate-soluble fraction, containing the phenolics/neutrals fractions, is then separated and washed with water to remove the remaining water-soluble carbohydrate and carbohydrate-derived materials, preferably in a 1:6 to 1:1, water:oil weight ratio. The ethyl acetate-soluble fraction is then further extracted with an aqueous metal bicarbonate solution, preferably a 5% by weight aqueous solution of sodium bicarbonate. The pH of the bicarbonate extraction solution is preferably maintained at approximately 8-9.5, and a 6:1 to 0.5:1 bicarbonate solution:oil weight ratio is preferably utilized. The aqueous bicarbonate layer extracts the strong organic acids and highly polar compounds, and the remaining ethyl acetate-soluble layer contains the phenols and neutral fractions. This ethyl acetate-soluble layer is then separated, and the ethyl acetate solvent is evaporated using any known evaporation technique, including vacuum evaporation techniques. The dried phenolics/neutrals fraction typically contains 0.5-1% of water with traces of ethyl acetate. Table II illustrates typical yields for various pine sawdust fast-pyrolysis oils and fractions of oils obtained during different test runs as well as for Douglas fir bark fast-pyrolysis oils.

TABLE II
Yields for Various Pyrolysis Oils

| Pyrolysis Oil | EtOAc Insol. | Water Sol. | Organic Acids | Phenolics/Neut | |
|---|---|---|---|---|---|
| Pine sawdust | 42.8 | 24.7 | 5.7 | 21.3[a] | |
| Pine sawdust | 28.2 | 39[c] | 6.1 | 26.7[b] | |
| Combined pine oil[d] | 22.8 | 28.9 | 6.7 | 25 | |
| Pine sawdust | 41[e] | 27.2 | 6.3 | 26 | |
| Douglas fir bark | 0 | 12.1 | 15 Solids: 2.9 | Phenolics: 47.8 | Neutrals: 15.6 |
| Douglas fir bark | 0 | ND* | 19 Solids: 4.8 | Phenolics: 50.8 | Neutrals: 17 |

[a]Phenolics: 16.5; Neutrals: 9.5
[b]Phenolics: 16.5; Neutrals: 6.0
[c]Water solubles by difference
[d]From two condensers
[e]EtOAc insolubles by difference
*Not Determined As indicated in Table II, the aqueous alkali metal bicarbonate solution utilized to extract strong organic acids and highly polar compounds further purifies the phenolics/neutrals fractions. While any suitable alkali metal bicarbonate solution may be utilized, the preferred solution is selected from sodium bicarbonate, potassium bicarbonate, lithium bicarbonate and ammonium bicarbonate, with sodium bicarbonate being the preferred and most optimal solution. From the aqueous bicarbonate solution, it is possible to isolate a fraction rich in organic acids as a by-product. In this instance, the aqueous layer can be neutralized, for example with 50% by weight of phosphoric acid (although other acids can be used) saturated with sodium chloride, and extracted with ethyl acetate. It is possible to then evaporate the solvents and isolate the remaining fractions as well.

The phenolics/neutral fraction can be further fractionated into isolated phenolics and neutrals if desired. This can be accomplished by utilizing a 5% by weight solution of sodium hydroxide in a volume ratio of 5:1 of solution:extract. The aqueous layer is then acidified to a pH of about 2 utilizing a 50% solution of phosphoric acid (although other acids can be used). It is then saturated with sodium chloride and extracted with ethyl acetate. Evaporation of the solvent leads to the isolation of the phenolics fraction; evaporation of the initial ethyl acetate solution freed from phenolics leads to the neutrals fraction. It should be noted, however, that the present invention does not require this separation of the phenol from the neutral fractions, and it is in fact this aspect of the present invention which makes the present process so economical. In the past, as previously indicated, the phenolics have always been the desired end-product, and sodium hydroxide has typically been utilized in such process treatment. This is unnecessary with the process of the present invention, since it has been discovered that the combined phenolics and neutrals fraction composition is sufficiently pure to function by itself in the formation of adhesive resins.

The process of the present invention can be operated in both batch mode as well as in a continuous mode. In the batch mode embodiment, the whole oils are extracted with ethyl acetate and then washed with water. Following the water wash, the composition is then washed with the aqueous sodium bicarbonate to eliminate the acidic components, which come from pyrolysis of the carbohydrate fraction and would be deleterious to the resins. In a continuous operation, the pyrolysis oils is preferably extracted simultaneously with water and ethyl acetate, and then the ethyl acetate's soluble fraction is extracted countercurrently with the aqueous bicarbonate solution. The whole ethyl acetate fraction, which includes both phenolic and neutrals compounds, is then utilized as a feedstock for resins after solvent evaporation.

EXAMPLE I 1.0 kg of fast-pyrolysis oil derived from pine sawdust was dissolved into 1 kg of ethyl acetate. After filtration of the solution, this solution then separated into two easily identified and separated phases. The ethyl acetate-soluble phase was then isolated, and 0.8 kg of water was added to this phase. The resulting water-soluble fraction was isolated and saved for further processing. 2 kg of 5% sodium bicarbonate solution was then added to the ethyl acetate-soluble fraction, and the aqueous phase therefrom was saved for further processing. This aqueous phase was the acids-soluble fraction. The resulting washed ethyl acetate-soluble solution, containing the phenol and neutral fractions, was then solvent evaporated to remove the ethyl acetate solvent. The yield of phenolics/neutral was 31% by weight based on the dry oil.

The remaining ethyl acetate-insoluble fraction was solvent evaporated and yielded a weight percent of the starting dry oil. The aqueous wash yield after solvent evaporation was 39 weight percent of the oil. The aqueous bicarbonate solution was neutralized with a 50% phosphoric acid solution, and after saturation with sodium chloride, the organic phase was extracted into ethyl acetate. After solvent evaporation, the acids fraction yield was approximately 7 weight percent.

EXAMPLE II 9.5 kg of fast-pyrolysis oils derived from pine sawdust were dissolved into 10 kg of ethyl acetate. After filtration, this solution settled into two easily identified and separated phases. 1.8 kg of water was then added to the ethyl acetate-soluble phase, and this solution was then separated into two easily identified and separated phases. The resulting water-soluble fraction was saved for further processing, and the other ethyl acetate-soluble fraction was then admixed with 8.9 kg of a 5% sodium bicarbonate solution. The aqueous phase of this solution was then separated and saved for further processing, which was the acids-soluble fraction. The resulting washed ethyl acetate-soluble solution, containing the phenolics/neutral fraction was separated, and the solvent was then evaporated. The yield of the phenolics/neutral fraction was 30% by weight based on dry oil.

Using a procedure similar to that described above in Example I, the mass balance of the fractionation was determined as follows: the ethyl acetate insoluble fraction comprises 21 weight percent, the water-soluble fraction comprises 31 weight percent, and the organic acids comprise 7.2 weight percent.

EXAMPLE III

The fractionation of Douglas fir pyrolysis products which are solids at room temperature, was similar to that described for pine. 4.6 kg of Douglas fir fast-pyrolysis product were dissolved into 9.8 kg of ethyl acetate solution. No ethyl acetate insoluble fraction was observed. The whole solution was then extracted with 12 kg of a 5 weight percent aqueous sodium bicarbonate solution. The ethyl acetate-soluble solution contained 68 weight percent of phenolics and neutrals. The phenols and neutrals were then separated by extraction with 11 kg of a 5 weight percent aqueous solution of sodium hydroxide. From the ethyl acetate solution, 17 weight percent of neutrals were obtained. The alkaline aqueous solution containing the phenolics was acidified with 50% phosphoric acid (although other acids could have been used). This solution was then saturated with sodium chloride and extracted with ethyl acetate to yield 50.8 weight percent for the phenolics fraction upon solvent evaporation. In the extraction with aqueous bicarbonate solution, a precipitate was formed (5 weight percent) along with the soluble acids fraction of 19 weight percent. The data for the fractionated materials are provided in Table II above.

EXAMPLE IV

Fast-pyrolysis oil derived from pine sawdust also o fractionated on a continuous basis. This continuous process utilized, but is not limited to, a 6-stage system of mixer tanks and settling tanks. The oil, ethyl acetate and water were mixed and allowed to settle, with the organic phase being sent on to multi-stage extraction with 5 weight percent aqueous sodium bicarbonate solution with each extraction stage having a separate settler tank. The bicarbonate extraction was run countercurrent to the flow of the organic phase. The aqueous fractions, that is the combined ethyl acetate insoluble and water-soluble fractions, the aqueous bicarbonate solution, and the organic phase were all collected and processed as described above. Conditions of the extraction included the following: oil flow, water flow, ethyl acetate flow, and aqueous bicarbonate flow rates were 10, 6, 34 and 35 mL/min, respectively. It should be noted, however, that the countercurrent continuous extraction process is not limited to these flow rates. The yield of phenolics/neutrals fractions composition was about 20% based on the oil flow rate and phenolics/neutrals isolated fractions. A total of 20 kg of oil was fractionated in this way. Variations in flow rates and number of settler and mixer tanks, however, can yield different proportions of materials. Phase separation was readily accomplished within the settlers.

Analysis of the products for intermediate stages of extraction revealed that 1-3 stages of bicarbonate extraction may be used. Turning from the Examples given above, the fractionation scheme described above allowed the isolation of 21% to 31% of the starting pine oils as a phenolics/neutrals fraction, or overall yields of 12-21% based on starting dry wood. This fraction consisted of approximately 73% phenolics, extractable from sodium hydroxide solution from an ethyl acetate solution, and 27% neutrals. The total yield of phenolics/neutrals fraction isolation is reproducible as shown by the runs in Table II above.

The typical oil contained 6.2% phenolic hydroxyl and 0.4% carboxylic acid contents by weight ranges. Ranges of 5 5-6.5% phenolic hydroxyl and 0.1-0.6% carboxylic acid contents are expected for the different starting feedstocks. The phenolics/neutrals fraction included about 6.6% phenolic hydroxyl content and no carboxylic acid content. Expected ranges for phenolics/neutrals are 6.0-12% depending on the feed. The acids fraction included about 9.2% phenolics and 0.9% carboxylic acid contents. Ranges for various feedstocks are 5-10% for phenolics and 0.5-3% carboxylic acid contents.

In characterizing the resultant phenol compositions, the apparent molecular weight distributions obtained from gel permeation chromatography on polystyrene-divinylbenzene copolymer gels (50 Angstrom) with tetrahydrofuran as solvent, indicated that the phenolics fraction had components ranging from the monomeric substituted phenols (around 150) to oligomers (up to several thousand in molecular weight). The acids and neutrals had the lowest molecular weight components. From molecular beam mass spectra of the phenolics/neutrals fractions, a number of phenolic compounds were detected: guaiacol (2-methoxyphenol) m/z 124; catechols m/z 110; isomers of substituted 2-methoxyphenols with alkyl groups such as methyl (m/z 138), vinyl (m/z 150), 3-hydroxy-propen(1)-yl (m/z 180), allyl (m/z 164), hydroxyethyl (m/z 168), and ethyl (m/z 152), most likely in the p-position. In addition, carbohydrate-derived compounds were present such as furfural alcohol and a number of other furfural derivatives.

From proton nuclear magnetic resonance spectrum of the phenolics/neutrals fraction, of the total intensity, the aromatic protons (6.5-10 ppm) constituted 52%, the aliphatic (1.5-3.5 ppm) about 20%, and the methoxy region and oxygenated and side-chain region (3.0-4.2 ppm) constituted 30%. This was in agreement with the description from the molecular beam mass spectra of mixtures of phenolics with substituted groups. The carbon-13 nuclear magnetic resonance spectra confirmed this data.

Bark derived phenolics have a very high phenolic hydroxy content (7.4-11.5%) depending on pyrolysis conditions (steam to nitrogen carrier gas) and therefore are very suitable for adhesive formulation replacing phenol at greater than a 50% level.

As previously indicated, a principal purpose of producing the phenolics/neutrals fractions is to provide a substitute for pure phenol in the production of resins and the like. Specifically, resoles, which are phenol-formaldehyde resins formed under alkaline conditions for gluing wood, were produced and compared to resoles utilizing standard formulations of commercially available phenol.

Of the various fractions of pyrolysis oil, only the phenolics/neutrals fractions gave a positive gel test under the above conditions. In preliminary gel testing of the phenolics/neutrals extract, one gram of para-formaldehyde was arbitrarily added to 4 grams of the extract. The pH of the extract was adjusted by adding 0.2-1.0 mL of 50% by weight sodium hydroxide. There appeared to be a strong buffering of the pH by the extract at a pH 9.5. Cascophen 313 was used for comparison. At 0.5 mL of added sodium hydroxide, the gel time of the phenolics/neutral fraction was much shorter than that of the Cascophen, with a gel time of only 29% that of Cascophen at 124° C. At 112° C., it was 34%, while at 101° C. it was 46% of Cascophen. At the original pH of 3 of the phenolics/neutrals fractions, there was no gelling of the mixture even at 132° C. with the same amount of added paraformaldehyde.

Figure 2:
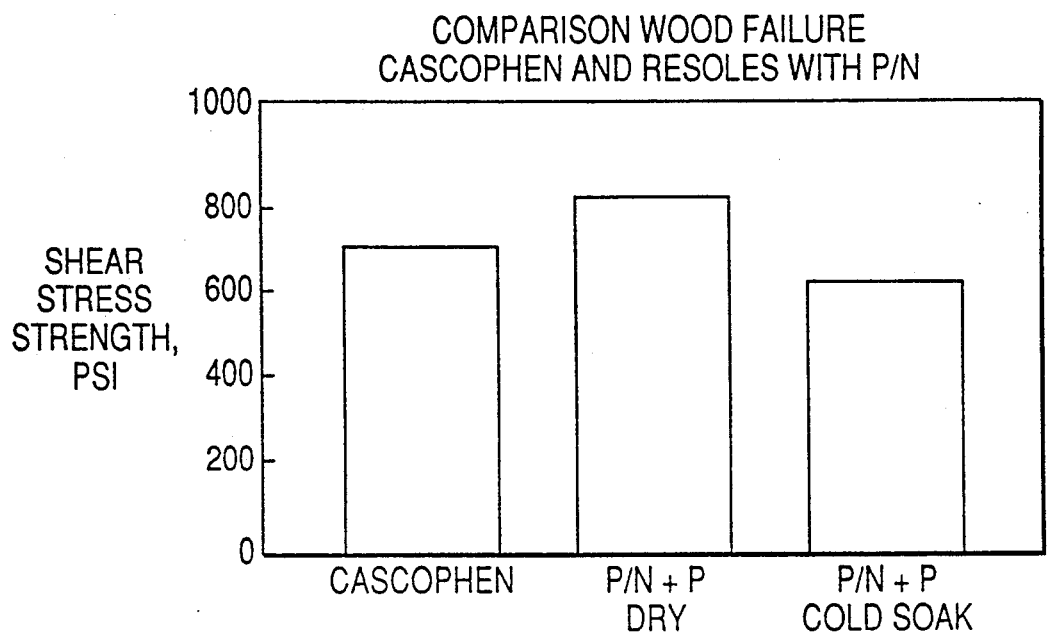
FIG. 2 is a graph illustrating shear stress strength of resin adhesives produced using the phenol and P/N end-products of the present invention compared to a commercial product.

Resoles have also been made utilizing a 50% replacement of phenol with the phenolics/neutral fractions produced by the process of the present invention. FIG. 2 discloses a comparison of shear stress strength between Cascophen and resoles produced with the phenolics/neutrals fraction of the present invention. Specimens were tested after a cold water soak (rightmost bar) and met test requirements. As can be seen from FIG. 2, the Cascophen showed a shear stress strength in psi of approximately 700, while the resole with the phenolics/neutral fraction produced from the present invention showed a strength of approximately 800 psi, significantly higher than Cascophen. Moreover, the resole produced from the phenolics/neutrals fraction of the present invention illustrated a cold soak strength of approximately 600, which is considerably higher than the standard 500 which has generally been set for existing products such as the Cascophen. The tests performed used the British standard 1204; Part 1:1964, and the testing of 10 specimens per evaluation. Thus, FIG. 2 illustrates the fact that the shear strength of resins produced by substituting 50% of the phenols therein with the phenolics/neutral fraction produced from the present invention are in fact stronger than phenol-formaldehyde resins utilizing pure phenol.

It has been found that useful resins may be obtained by substituting from about 25 to about 75 weight percent of the phenol normally present in a resole resin with the P/N fraction of the invention. Resins have been prepared with from about 5 to about 75% by weight, and this is preferred. However, about 15 to about 50% by weight is most preferred.

Figure 3:
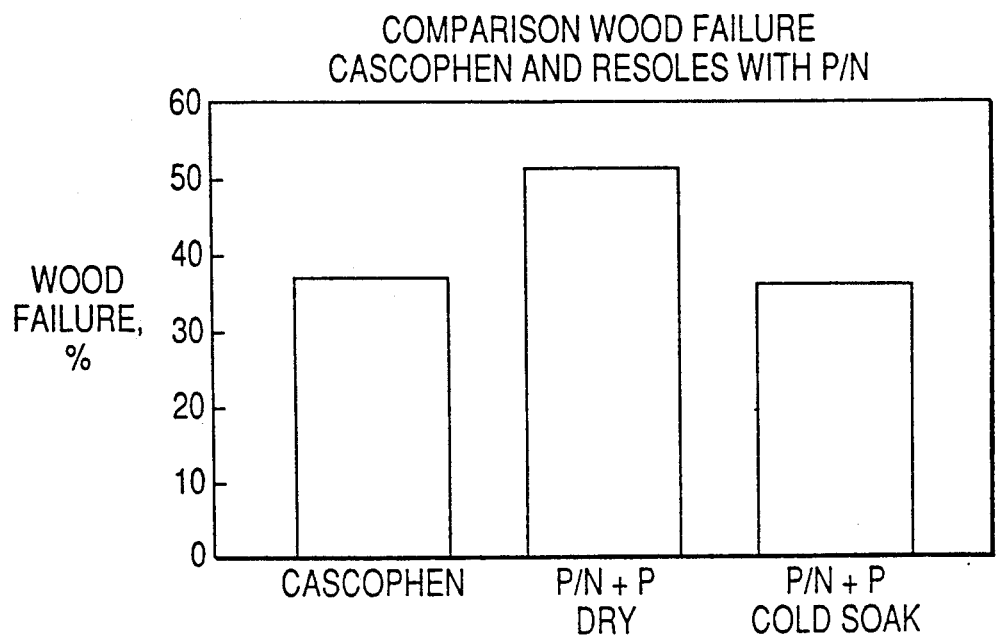
FIG. 3 is a graph illustrating wood failure test results of resole adhesive resins produced using the phenol and P/N end products of the process of the present invention compared to a commercial adhesive product.
Figure 4:
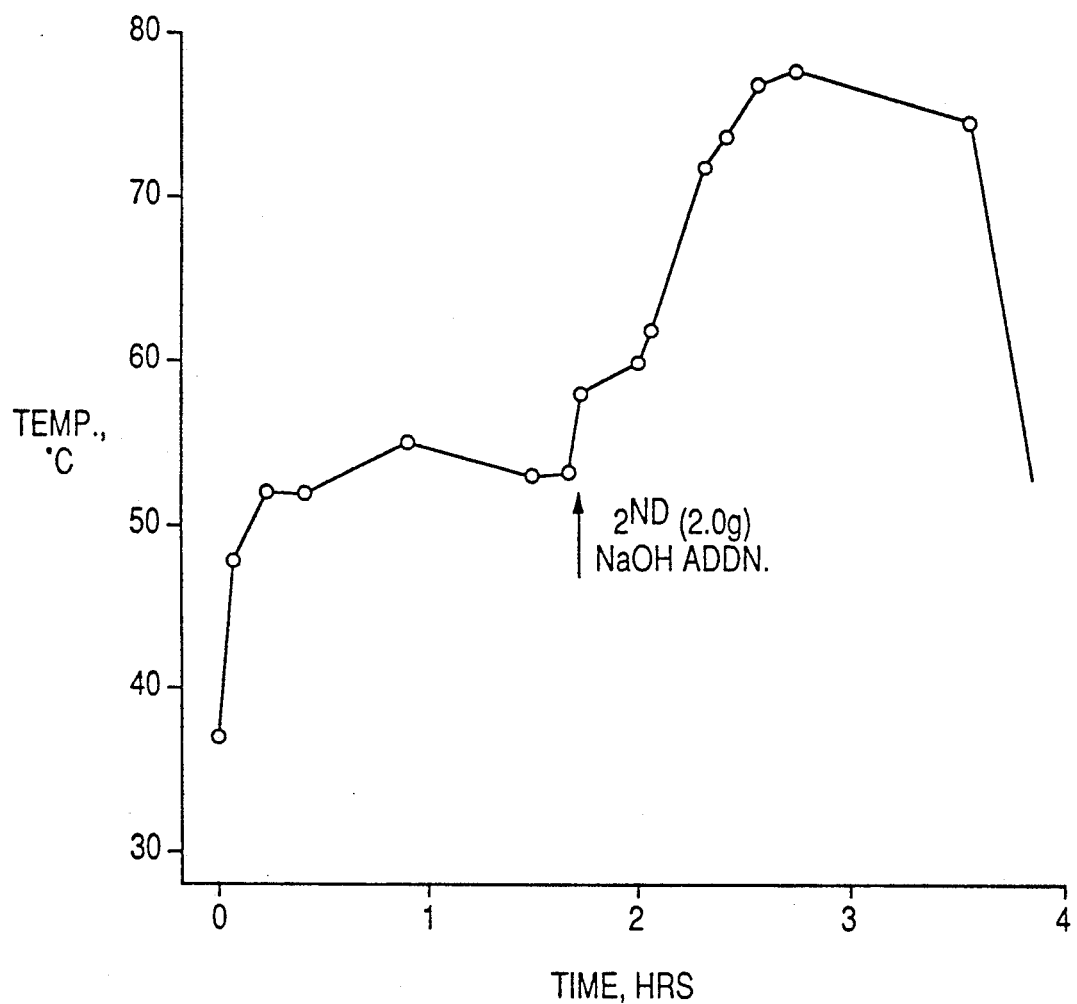
FIG. 4 is a graph showing the time/temperature relationship for the preparation of resole resins according to one aspect of the invention.
Figure 5:
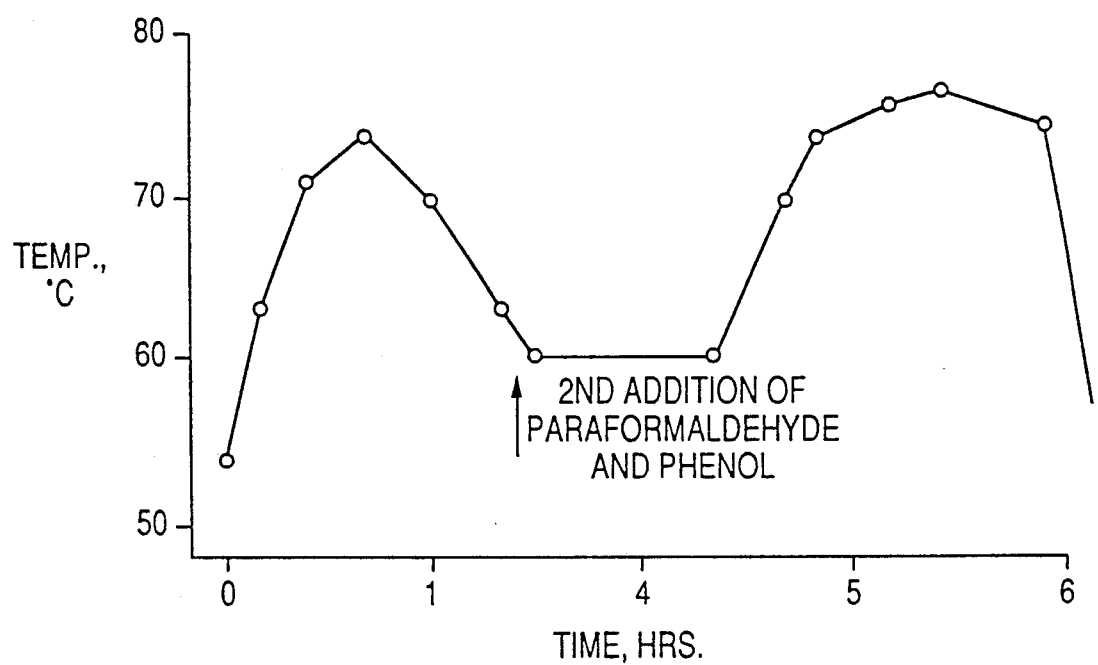
FIG. 5 is a graph showing the time/temperature relationship for the preparation of resole resins according to another aspect of the invention.

Referring to FIG. 3, wood failure tests are compared between the Cascophen and resoles having the phenolics/neutrals fractions produced from the present invention. To interpret FIG. 3, it should be understood that it is preferred to have a wood failure, not a resin failure. Thus, if the wood fails, the resin is deemed to be good, and if the resin fails, it is deemed not to be good since the resin has actually separated. Thus, it is desirable to have a higher wood failure percent in order to show resin strength. Referring to FIG. 3, it should be clear that the Cascophen samples had a wood failure of approximately 38%, while the resin produced by substituting 50% of the phenolic portion with the phenolics/neutral fraction from pyrolysis oils was well over 50%, illustrating a significant difference in resin strength capability. Moreover, the cold soak test results illustrated that the resole having the phenolics/neutrals fraction produced from the present invention had a cold soak rating the same as a non-cold soak rating of the Cascophen. Thus, these tests further indicated that resole resins produced by substituting 50% of the phenol with the phenolics/neutrals fraction produced from the present invention are considerably better in function and strength than standard commercially available products. The tests performed used the British standard 1204: part 1:1964, and testing of 10 specimens per evaluation.

With respect to the economic benefits of the present invention, historical petroleum derived phenol costs range from $0.25 to $0.45 per pound (1981-1991) depending on petroleum costs and the state of the economy, particularly housing, the major market segment that employs resole phenolic resins. The average cost of phenol in these past eleven years is $0.34/pound. Prior to the present invention, the main competition has been the lignin-derived substitutes from commercial pulping processes. Kraft lignins have to be made chemically more reactive to replace phenol in phenol-formaldehyde resins with similar performance. These commercial products are sold as resin co-reactants, and their price ranges from $0.33-$0.85 per pound depending on the reactivity needed (based on kraft lignins). Less expensive products are available from the process of the present invention and are co-reactants with the ability to replace about 50% of the phenol in phenol-formaldehyde resins as described above. Indications are that for molding compounds, plywood, particle board, oriented board, paper overlays and other similar adhesive resins, 50% phenol replacement would provide a very similar performance to the commercial phenolic adhesives, and in fact would give a better performance as illustrated and described above in FIGS. 2 and 3. However, there is a significant cost reduction factor in that the phenol-formaldehyde fractions produced from the P/N composition of the present invention have an amortized cost projection at approximately $0.16 per pound compared to $0.30 to $0.40 per pound for commercial phenol. If the lignocellulosic starting material is bark, this cost is even less because the yield of phenolics from the bark is higher than that of sawdust or pine. Plant sizes were 250 to 1000 tons of feedstock per day, 15% return on capital, plant life of 20 years, and waste sawdust at $10.00 per dry ton.

As described above, the most developed application for the end products of the present invention is the replacement of 50% and potentially more of phenol in phenol-formaldehyde resins for use as molding compounds, foundry, and shell moldings. Other potential applications for the resulting product of the process of the present invention include the replacement of phenol in softwood and hardwood plywood resins, the insulation market, composite board adhesives, laminated beams, flooring and decking, industrial particle board, wet-formed hard boards, wet-formed insulation boards, structural panel board, and paper overlays. Alternative adhesive systems from the carbohydrate-rich fractions of the present invention could also be made.

In addition, another product that can be derived from the other fractions of the pyrolysis oils is an aromatic gasoline. Passage of vapors of these compounds over zeolite catalysts produces high octane gasoline, as more clearly discussed in "Low-pressure upgrading of Primary Pyrolysis Oils form Biomass and Organic Waste", in Energy from Biomass and Wastes, Elsevier Applied Science Publishers, London, pp. 801-830 (1986).

A final advantage to the present invention is that about one-third of the usual amount of formaldehyde employed in conventional phenolic adhesives is necessary in producing adhesives wherein 50% of the phenol is substituted with phenolics/neutral fractions provided by the present invention. Since there is significant environmental concern over formaldehyde emissions from resins, the products resulting from the process of the present invention therefore become very important from this context.

As can be seen from the above, a novel process for fractionating fast-pyrolysis oils to produce phenolic compounds-containing compositions having P/N fractions contained therein suitable for manufacturing phenol-formaldehyde resins are disclosed. The process is simple and economic, and can be used in either batch or continuous mode operations. The resulting P/N composition can be subsequently utilized to produce resole resins of comparable or superior performance characteristics relative to standard phenol-formaldehyde resins yet the pyrolysis-derived phenolic feedstocks are projected to cost less than half of the cost of petroleum-derived phenol. Moreover, these resulting resins have numerous different types of applications, and the cost benefits alone are significant.

EXAMPLE V (Run 109)

Using 24 kg of dry, Colorado pine sawdust as feed for the fast pyrolysis vortex reactor with steam as the carrier gas at a steam-to-biomass ratio of 1.5, 60.2 kg of pyrolysis condensates (including water) were prepared, which had both an aqueous and an organic phase. The average measured temperature of the carrier steam was 700° C. at 98 psia, upstream of the supersonic nozzle in the ejector. The average measured temperatures of the vortex reactor wall were 610° C. in the first third, 608° C. in the middle third and 626° C. in the last third of the reactor. Immediately downstream of the vortex pyrolysis reactor was a char cyclone, followed by a long, heated transfer tube (the process stream had a gaseous residence time of about 0.4 seconds in this tube), a second char cyclone, and then the first condenser. The average measured temperatures of the pyrolysis process stream at the entrance to the transfer line and at the six equally spaced locations down the transfer line were 493°, 544°, 526°, 502°, 489°, 496°, and 495° C.

To remove the residual organic phase from the condensate collection equipment, 1 kg of ethyl acetate was used (the weight of the wash ethyl acetate is included in the condensate weight). These condensates were similar to those used in Example IV, but also included the condensed carrier steam. The organic phase was relatively viscous, which could coat the glass membrane of the pH electrodes, and thus cause erroneous pH measurements. The aqueous phase (56.2 kg) was decanted and slowly neutralized by the addition of 2.2 kg of dry, solid sodium bicarbonate until an indicated pH of 6.8 was reached. This avoided the fouling tendencies of the pH electrode by the organic phase during the addition of the sodium bicarbonate. The neutralized aqueous material was mixed overnight, at which time the measured pH had risen to 7.5 (due to the loss of dissolved carbon dioxide). The organic phase was dissolved in 5 kg of ethyl acetate to facilitate transfer from its container to the mixer. The organic solution was then mixed into the previously neutralized aqueous phase to result in a slightly lowered pH of 7.3, which rose to 7.4 after mixing overnight. Thus, the previously neutralized aqueous phase solution was used to neutralize the small amount of acidity present in the organic phase. This minimized the loss of ethyl acetate in the evolved carbon dioxide. No significant formation of an organic precipitate was reported during the neutralization and extraction sequence.

The extraction of the phenolic-containing/neutrals could have been accomplished in any of a number of ways known to one skilled in the art, but in this case, the neutralized, two-phase suspension was then metered into a liquid extraction system having counter-current flow through three mixer-settlers in series. Each mixer had a volume of 250 mL and each settler had a volume of 3000 mL. The neutralized feed was fed at 50 mL per minute and the ethyl acetate solvent was fed at 35 mL per minute, although these rates are not meant to be limiting. The phenolics and neutrals (P/N) materials were extracted into the organic phase with the use of 0.7 volume of ethyl acetate per volume of mixed-phase neutralized condensates. A total of 2.6 kg of ethyl acetate was used per kg of dry wood feed. The ethyl acetate was evaporated from the organic phase to result in about the same yield of P/N material as was obtained in Example IV, 0.17 kg P/N per kg dry wood feed.

EXAMPLE VI (Run 116)

In an integrated, commercial application, it is anticipated that the aqueous phase, containing the neutralized organic acids and other water soluble organics, may be incinerated in a furnace. This would both dispose of the contaminated water, as well as, recover the sodium bicarbonate. However, from such a furnace, it is well known that the sodium salt recovered is soda ash (sodium carbonate) rather than sodium bicarbonate. An additional process step is required to convert the recovered sodium carbonate to sodium bicarbonate, i.e. carbon dioxide gas is bubbled through an aqueous solution of sodium carbonate. This additional step is expensive as evidenced by the fact that the commercial value of sodium bicarbonate is about three times that of sodium carbonate. This carbonation process requires the addition of a large amount of water to form the aqueous solution, due to the relatively small solubility of sodium bicarbonate in water. As discussed above, this additional water is detrimental to the operability of the process. In addition to being cheaper, only half as much sodium carbonate is required to neutralize a given amount of acidic material compared to sodium bicarbonate on a molar basis (0.63 times less on a weight basis). Coupled with the lower cost per pound of sodium carbonate, this lowers the cost of the raw materials by a factor of 5 to neutralize with sodium carbonate rather than sodium bicarbonate.

Therefore, it would be advantageous to be able to use the cheaper sodium carbonate to neutralize the pyrolysis condensates. However, the pH of aqueous sodium carbonate is much higher at 11.6, as compared to that of sodium bicarbonate at only 8.4. It was expected by those skilled in the art, that some of the phenolic constituents of the pyrolysis condensates would react with the sodium carbonate to form sodium phenolates, which are water soluble and therefore would not be as well extracted into the ethyl acetate solvent phase. In addition, base-catalyzed condensation reactions, that are not advantageous, could take place at a higher pH, thus altering the proportion of low- and high-molecular weight phenolic products in the material.

However, it has been found that by slowly adding dry, basic sodium carbonate to the acidic pyrolysis condensates until only a pH of about 7 is reached, that the phenolic constituents are still primarily extracted into the organic solvent phase, rather than forming the water-soluble phenolates. This unexpected observation allows the use of the more basic sodium carbonate, or other basic materials that may be advantageous to replace the sodium bicarbonate in the neutralization process, which could result in a significant cost savings or other advantages.

Sixty-nine kg of pyrolysis condensates (including water) were formed by the fast pyrolysis of 27 kg of dry Colorado pine sawdust in the vortex reactor using steam as the carrier gas at a steam-to-dry-sawdust ratio of 1.2 to 1.8 and at a sawdust feeding rate of 11 to 16 kg per hour. The steam was at 88 psia and 700° C. prior to expansion through the supersonic orifice of the ejector at the entrance of the vortex reactor. The walls of the vortex reactor were at a nominal 625° C. to result in an average pyrolysis stream exit temperature of 530° C. In the transfer line between the two char cyclones, the average measured gas temperature at the entrance and at six equally spaced locations were 498°, 520°, 527°, 500°, 490°, 463°, and 455° C., respectively. The gas phase residence time in the transfer line was about 0.4 seconds.

To aid in equipment cleanup 4 kg of ethyl acetate were added. An additional 9 kg of ethyl acetate was added to transfer the organic phase into the mixer for neutralization. For neutralization, 1.5 kg of dry sodium carbonate was added to the two-phase suspension to result in an initial pH of 6.8. After two days, the pH had dropped to 6.2 and an additional 0.1 kg of sodium carbonate was added to result in the final pH of 6.8. Care was taken during the neutralization to keep the pH electrode clean and the calibration was checked after each use. The amount of solid precipitate was 0.026 kg per kg of sawdust fed. Although any of several well known methods of extraction could have been utilized, this neutralized material was then extracted in the three-stage counter current extraction system described in Example V. The total weight of ethyl acetate used was 3.0 kg per kg of dry wood fed. The yield of P/N material was 21 % by weight of the feed, higher than that obtained in Example V, but similar to yields obtained in batch mode operation.

EXAMPLE VII (Run 126)

Using 125 kg of Southern pine sawdust, 258 kg of pyrolysis condensates (including water) were produced using steam as the carrier gas at 1 to 1.1 kg steam per kg of dry sawdust in the vortex pyrolysis reactor. The feed rate was 18 to 20 kg dry feed per hour. The pyrolysis temperatures were as in the above examples, except that the average measured temperature of the pyrolysis stream at the exit of the vortex reactor was 500° C. (stnd. dev. of 11° C.) and in the transfer line, between the primary and secondary char cyclones, the average measured temperatures at eight locations were 438° C. To more completely recover the condensed material from the equipment, 11.9 kg of ethyl acetate was used.

Two samples were made from the condensates produced. The first sample contained 87 kg of condensates. The aqueous phase was decanted and neutralized to a pH of 7.4 from an initial pH of 2.7 with 1.8 kg dry sodium carbonate. To the organic phase, 28.5 kg of ethyl acetate was added to make a very low viscosity solution. This solution was then added to the previously neutralized aqueous phase to make the two-phase suspension to feed to the continuous flow, countercurrent extraction system. After mixing the two phases together, a significant amount of solid precipitate formed, which was skimmed off from the top of the suspension. Although, the extraction could be carried out in any of several manners, in this case, the extraction system consisted of three mixer/settlers in series, with the mixers having a volume of 750 mL and the settlers having a volume of 3000 mL. The feed rates were 300 mL per minute for the neutralized feed and 210 mL per minute for the ethyl acetate, although one skilled in the art recognizes that one could vary these rates considerably and still obtain a usable product.

The second sample of 179 kg of pyrolysis condensates (including water) was mixed with 63 kg of ethyl acetate to keep the organic phase fluid and easily suspended in the mixer. This two-phase suspension was then neutralized from an initial pH of 2.9 to a final pH of 6.8 by the addition of 4.0 kg of sodium carbonate. At this time a solid precipitate floated to the top of the suspension, where it was skimmed off. The amount of precipitate recovered from the second sample of this example was judged to be proportionately similar to that observed in the first sample. Thus, demonstrating that the order of neutralization relative to the addition of ethyl acetate did not have a marked effect on the preparation of the condensates for extraction nor on the formation of the solid precipitate, which must be removed prior to extraction to avoid operational problems. The recovered precipitate was found to be about 6 wt % of the sawdust feed.

Although any number of different methods could have been used to contact the neutralized suspension in countercurrent flow with ethyl acetate solvent, a three-stage mixer/settler system was used having the same dimensions and nominal flow rates noted for the other sample described above in this example.

The organic phase was mixed with that from several other batches to result in an average yield of phenolics-containing/neutrals of 0.19 kg per kg of dry feed.

EXAMPLE VIII (Run 121)

Using steam as the carrier gas in the vortex pyrolysis reactor, 35 kg of dry Southern pine sawdust was pyrolyzed to produce 77 kg of condensates (including water). The carrier gas to sawdust weight ratio was 1.2 at a sawdust feeding rate of 16 kg per hour. The average steam temperature was 690° C. measured upstream of the ejector nozzle at 90 psia. The average temperatures measured in the vortex reactor wall were 570° C. in the first third, 600° C. in the middle third, and 630° C. in the last third. The measured average temperature of the pyrolysis process stream as it exited the vortex reactor was 495° C. with a standard deviation of 4° C. (128 measurements). The transfer line between the primary char cyclone and the secondary char cyclone was heated and the average measured temperatures of the pyrolysis stream were 505° C. (128 measurements at each of 6 axial locations with a standard deviation of 23° C.) with a calculated residence time of 0.4 seconds. However, since chemical kinetics are exponential with temperature, it is important to recognize that it is the instantaneous temperatures of the pyrolysis process stream, not the overall average temperature, that are important. The average temperatures at the exit of the vortex reactor, the transfer line entrance, and the six equally spaced locations of the transfer line itself were 500°, 485°, 525°, 530°, 515°, 505°, 490°, and 477° C. respectively.

A 49 kg sample of the mixed suspension of condensates was neutralized and extracted. To aid in the transfer of the thick organic phase and to lower the viscosity of the organic phase during neutralization, 16 kg of ethyl acetate was added to the two-phase suspension prior to neutralization. To neutralize the suspension to a pH of 6.9 from the initial pH of 2.7 required 1.1 kg of sodium carbonate. Only a very small amount of solid precipitate, 0.0009 kg per kg sawdust, was observed after the neutralization (about 65 times less than for Example VII). Apparently the higher process temperatures during the residence time in the heated transfer line were sufficient to achieve a thermally induced change in material, which otherwise would have produced a solid material, which would have precipitated in the extraction step. This change presumably lowered the molecular weight or otherwise made that material, which would have precipitated, more soluble in the ethyl acetate/water solvent system.

Although any number of different methods could have been used to contact the neutralized suspension in countercurrent flow with ethyl acetate solvent, a three-stage mixer/settler system was used having the same dimensions and nominal flow rates noted for Example VII.

EXAMPLE IX (Run 133)

In all of the above examples, the sawdust feed had been completely dried at 105° C. and was fed to the vortex reactor while still at about this temperature. This results in an equilibrium moisture content in the feed of less than 1%. In a commercial process, it may not be feasible to achieve this low level of moisture, although it may be desirable to do so in order to minimize both the heat required for pyrolysis and the amount of waste water for disposal. To evaluate the effect of residual moisture in the feed, the moisture in the as-received sawdust was measured and then adjusted to result in 8% moisture in the feed. To avoid moisture losses prior to pyrolysis, the feed was not preheated, but rather fed at ambient temperature into the vortex reactor. The vortex reactor was operated as in the above examples, but with 39.5 kg of Southern pine sawdust fed at a lower rate of 12.9 kg per hour and a steam-to-biomass ratio of 1.7. The heated transfer line was maintained at a very uniform, measured temperature of 500° C. within 11° C.

Although any number of different methods could have been used to contact the neutralized suspension in countercurrent flow with ethyl acetate solvent, a three-stage mixer/settler system was used having the same dimensions and nominal flow rates noted for Example VII.

ADDITIONAL FRACTIONATION EXAMPLES

This information is summarized in Tables III, IV, and V, which also contains examples of fractionation of other materials prepared similarly. In addition to the thermal severity conditions (temperature/time), the extraction severity is another important parameter varied. It is represented by the pH of the neutralization step, which is an approximate measure in the non-aqueous solvents-containing solutions employed.

Most of the examples of resoles prepared in the new procedures are from runs 121-140.

TABLE III

SUMMARY OF P/N PRODUCT PREPARATION AND CHARACTERIZATION FROM LIGNOCELLULOSIC FEEDSTOCKS SUBJECTED TO FAST PYROLYSIS AND SOLVENT FRACTIONATION

| P/N No. | Pyr. Run No. | Feedstock Carrier gas | Neutr. Mode | Extn. Type | Solv. Evpn. | Sample Code | $H_2O$ % | EtAc % | phOH % | Phenol equiv % |
|---|---|---|---|---|---|---|---|---|---|---|
|  |  |  |  |  | Phenol Alone |  |  |  | 18.1 | 100 |
| 1 | 110 | Redwood, N2 | Aq. Bic | Batch | RV @ 45° C. | XIV-80-PN | .3 | 3.8 | 7.2 | 39.6 |
| 2 | 82 | CO pine, N2 | Aq. Bic | Batch | RV @ 45° C. | XIII-27-PN | 2 | 5 | 6.8 | 37.6 |
| 3 | 101-2 | CO pine, N2 | Aq. Bic | C, FR1 | FF + RV @ 45° C. | XV-159-PN | .6 | 4 | 6.8 | 37.3 |
| 4 | 108 | CO pine, steam | Dry Bic | C, FR1 | FF + RV @ 45° C. | XIV-48-PN | 1 | 9 | 5.7 | 32.7 |
| 5 | 109 | CO pine, steam | Dry Bic | C, FR1 | FF + RV @ 45° C. | XIV-84-PN | 2 | 5 | 5.3 | 30.8 |
| 6 | 113-4 | CO pine, steam | Dry Bic | C, FR1 | FF + RV @ 45° C. | XIX-12-PN | 1 | 5 | 6.7 | 36.9 |
| 7 | 116 | CO pine, steam | Dry Car | C, FR1 | FF + RV @ 45° C. | XIX-84-PN | 5 | 1 | 6.7 | 37.3 |
| 8 | 116 | CO pine, steam | Dry Car | C, FR1 | FF + RV 6% $H_2O$ | XIX-50-PN | 5 | .3 | 6.1 | 34.1 |
| 9 | 116 | CO pine, steam | Dry Car | C, FR1 | FF + RV @ 65° C. | XIX-51-PN | 1.8 | 1.5 | 6.1 | 33.8 |
| 10 | 118-9 | CO pine, steam | Dry Car | C, FR1 | FF + RV @ 45° C. | XIX-93-PN | 2 | 2 | 7.0 | 38.9 |
| 11 | 118-9 | CO pine, steam | Dry Car | C, FR3 | FF + RV @ 45° C. | BH-4-2-PN | 1 | 3 | 7.1 | 40.8 |
| 12 | 118-9 | CO pine, steam | Dry Car | C, FR2 | FF + RV @ 45° C. | BH-4-1-PN | 1 | 1 | 7.0 | 38.9 |
| 13 | 121 | So. pine, steam | Dry Car | Batch | RV small | XX-80-PN | .9 | 5.5 | 5.9 | 32.7 |
| 14 | 127 | So. pine, steam | Dry Car | Batch | RV small | XX-77-PN | 2.2 | 3.6 | 5.8 | 32.6 |
| 15 | 121-7 | So. pine, steam | Dry Car | C, FR6 | top RV/$H_2O$ @ 45° C. | XX-69-PN-RK | 2.8 | 1.5 | 6.2 | 34.3 |
| 16 | 121-7 | So. pine, steam | Dry Car | C, FR6 | FF + RV/$H_2O$ @ 55° C. | XX-84-PN-RK | 7.7 | 1.1 | 6.2 | 34.4 |
| 17 | 121-7 | So. pine, steam | Dry Car | C, FR6 | FF + RV/$H_2O$ @ 55° C. | XX84-Master | 7.7 | 1.1 | 6.2 | 34.4 |
| 18 | 121-7 | So. pine, steam | Dry Car | C, FR6 | FF + RV/$H_2O$ @ 55° C. | XX-84-PNLOT1 | 4.2 | 2 | 6.2 | 34.4 |
| 19 | 121-7 | So. pine, steam | Dry Car | C, FR6 | FF + RV/$H_2O$ @ 55° C. | XX-84-PNLOT2 | 5.9 | 1.9 | 6.2 | 34.4 |
| 20 | 121-7 | So. pine, steam | Dry Car | C, FR6 | top FF + WE | ARISTECH | .2 | .5 | 6.7 | 37.0 |
| 21 | 131 | So. pine, steam Montecello | Dry Car | C, FR6 | FF + RV/$H_2O$ @ 55° C. | XXI-71-PN | 5.6 | 1.7 | 5.9 | 32.6 |
| 22 | 132 | So. pine, steam Russelville | Dry Car | C, FR6 | FF + RV/$H_2O$ @ 55° C. | XXI-67-PN | 3.3 | 0.3 | 5.9 | 32.6 |
| 23 | 133 | So. pine, steam South Boston, wet | Dry Car | C, FR6 | FF + RV/$H_2O$ @ 55° C. | XXI-79-PN | 4.9 | 2 | 5.9 | 32.6 |
| 24 | 84 | Aspen, N2 | Aq. Bic | Batch | RV @ 45° C. | BH1-13B-PNA | .9 | 7.5 | 7.5 | 41.9 |
| 25 | 134 | So. pine, steam | Dry Car | C, FR6 | FF + RV/$H_2O$ @ 55° C. | 723-048-PN | 6.5 | 5.0 | 6.8 | 37.3 |
| 26 | 135 | So. pine, steam | Dry Car | C, FR6 | 2FF + RV/$H_2O$ @ 55° C. | 723-044-PN | 5.8 | 3.1 | 7.1 | 40.8 |
| 27 | 137-9 | So. pine, steam | Dry Car | C, FR6 | FF + RV/$H_2O$ @ 55° C. | 723-051-PN | 5.4 | 1.8 | 6.3 | 35.0 |
| 28 | 137-9 | So. pine, steam | pH 7.7 | DC, FR6 | FF + RV/$H_2O$ @ 55° C. | 723-055-PN | 9.0 | 1.8 | 5.7 | 31.5 |
| 29 | 137-9 | So. pine, steam | pH 2.3 | water | FF + RV/$H_2O$ @ 55° C. | 723-058-PN | 4.8 | 0.8 | 7.4 | 42.5 |
| 30 | 140 | Oak, steam | Dry Car | C, FR6 | FF + RV/$H_2O$ @ 55° C. | 723-063-PN | 8.3 | 0.4 | 6.5 | 35.7 |
| 31 | Waterloo | So. pine | Dry Car | C, FR6 | 2FF + RV/$H_2O$ @ 55° C. | 723-045-PN | 5.8 | 3.1 | 6.5 | 35.7 |
| 32 | Red Arrow | Maple, I | Dry Car | C, FR6 | 2FF + RV/$H_2O$ @ 55° C. | 723-046-PN | 8.8 | 1.8 | 6.2 | 34.4 |
| 33 | Red Arrow | Maple, II | Cry Car | C, FR6 | 2FF + RV/$H_2O$ @ 55° C. | 723-064-PN | 6.4 | 2.1 | 6.0 | 33.3 |

TABLE III-continued

EXPLANATIONS:

Detailed Method of Preparation of the P/N Product: Numbers 1 and 24 are described in Example I; Number 2 is described in Example II; Number 3 is described in Example IV; Number 5 is described in Example V; Numbers 7–12 are described in Example VI; Numbers 14–22 are described in Example VII; Number 13 is described in Example VIII; Number 23 is described in Example IX. All samples described are prepared in a manner described by one of these detailed Examples. Summary of conditions are given in the Table II, IV, and V.

Feed: CO pine is a mixture of Colorado Pines (mainly Ponderosa and Lodgepole); Locations for the Southern pines are indicated: South Boston, VA, Monticello, GA, or Russelville, SC. The main types of Southern pines include: loblolly, longleaf, shortleaf, and a minor species is slash. Runs 133–139 were performed with South Boston feed as well as the production of the P/N product from the Waterloo reactor. Red Maple was used in the production of products 31 and 32, and these runs were performed at Red Arrow.

Carrier Gas: Nitrogen or steam

Run No.: Pyrolysis Run Number.

Neutralization type: Type of base added - Aq. Bic = 5% aqueous $NaHCO_3$; Dry Bic = dry $NaHCO_3$; Dry Car = dry $Na_2CO_3$; base added to lower the pH to 6.4–7.8. One experiment, production of product PN number 29 did not neutralize only water washed. The phen olic content for this product is overestimated.

Extraction Type: Batch (small amounts, hand extractions in separatory funnels); C = semicontinuous; FR1 = base case flow rate - mixing time 3 min and 30 min settling time; FR2 = mixing time 1.5 min and 15 min settling time; FR3 = mixing time 1 min and 10 min settling time; FR6 = same times of FR3 but with double the vessel size for details see Table V.

Solvent Evaporation: RV = rotary evaporation; at 45° C. or at 55° C. as the bath temperature; FF = falling film evaporator; WE = Wiped film evaporator; this sample was removed from the topmost part of the container, and was not fully mixed as were the samples labeled XX-84. Prior to Wiped film evaporation and after evaporation, the P/N sample was heated with a heat gun for 10–15 min at about 85° C. in order to reduce viscosity and increase flow rate to transfer to containers. Sample XX-69-PN was also prepared from the topmost sample from the drum container. Samples labeled XX-84 were homogenized prior to rotary evaporation. Lot 1 and Lot 2 refer to two of many lots that were used to make the master lot; samples from these lots were identical within the experimental error to those of the fully homogenized batch.

Sample Code: Roman Numerals refer to Stuart Black's notebook number; following arabic number refers to page number in notebook; PN refers to PN product; GH samples refer to Bonnie Hames' notebook number (1st arabic number) and page number (second arabic number).

Samples marked with RK refer to the samples prepared as described, which were sent to Roland Kreibich for testing and returned from after gel time testing for comparative chemical characterization.

Water and Ethyl Acetate (EtAc) determinations by Gas Chromatography. Phenolic hydroxyl contents determined by conductimetric titration.

Phenol equivalence: phenolic OH % * (94/17) * 100.

TABLE IV

PYROLYSIS CONDITIONS

| P/N # | Run # | Recycle Loop Temp. °C. | Reactor Exit Temp. °C. | Reactor Pressure (in $H_2O$) | Avg. Vapor Cracker Temp. °C. | Vapor Cracker Res. Time in seconds | Steam to Biomass Ratio | Feed Rate (kg/h) | Product Distribution Wt. % Char | % of Feed Gas | Oil* |
|---|---|---|---|---|---|---|---|---|---|---|---|
| 1 | 110/$N_2$ | 351 | 463 | 40 | 407 | 0.60 | 1.74 | 14.4 | 24.2 | 10.3 | 65.5 |
| 2 | 82 | 376 | 476 | 46 | 382 | 0.71 | 1.38 | 13.0 | 16.0 | 9.7 | 74.3 |
| 3 | 101/$N_2$ | 370 | 491 | 55 | 350 | 1.01 | 2.05 | 10.0 | 16.6 | 10.7 | 72.7 |
| 3 | 102/$N_2$ | 434 | 504 | 63 | 397 | 0.84 | 2.32 | 10.0 | 17.4 | 12.2 | 70.4 |
| 4 | 108 | 447 | 496 | 61 | 451 | 0.52 | 1.28 | 17.0 | 14.0 | 10.2 | 75.8 |
| 5 | 109 | 450 | 496 | 63 | 491 | 0.40 | 1.68 | 13.0 | 9.9 | 11.8 | 78.3 |
| 6 | 113 | 463 | 527 | 63 | 443 | 0.58 | 1.84 | 11.0 | 10.0 | 16.8 | 73.2 |
| 6 | 114 | 442 | 518 | 67 | 455 | 0.57 | 1.59 | 12.7 | 10.3 | 10.2 | 79.5 |
| 7-9 | 116 | 430 | 530 | 62 | 493 | 0.43 | 1.11 | 17.5 | 12.0 | 12.0 | 76.0 |
| 10-12 | 118 | 388 | 470 | 63 | 482 | 0.43 | 1.18 | 17.0 | 15.9 | 8.9 | 75.2 |
| 10-12 | 119 | 345 | 470 | 57 | 505 | 0.42 | 1.22 | 16.6 | 15.1 | 9.8 | 75.1 |
| 15-20 (13) | 121 | 377 | 495 | 62 | 503 | 0.42 | 1.23 | 16.4 | 14.6 | 11.5 | 73.9 |
| 15-20 (14) | 127 | 386 | 498 | 74 | 413 | 0.48 | 1.25 | 20.0 | 13.5 | 14.1 | 72.4 |
| 15-20 | 122 | 368 | 510 | 70 | 438 | 0.57 | 1.25 | 16.0 | 13.1 | 13.6 | 73.3 |
| 15-20 | 123 | 358 | 491 | 67 | 428 | 0.58 | 1.20 | 16.7 | 14.2 | 10.4 | 75.4 |
| 15-20 | 124 | 363 | 484 | 65 | 442 | 0.55 | 0.83 | 24.0 | 14.9 | 9.0 | 76.1 |
| 15-20 | 125 | 362 | 489 | 64 | 440 | 0.55 | 0.88 | 22.6 | 15.1 | 11.3 | 73.6 |
| 15-20 | 126 | 385 | 500 | 71 | 415 | 0.45 | 1.28/1.15 | 21.1/17.4 | 13.4 | 14.2 | 72.4 |
| 21 | 131 | 410 | 520 | 55 | 497 | 0.49 | 1.09 | 19.7 | 13.7 | 12.6 | 73.8 |
| 22 | 132 | 409 | 490 | 80 | 492 | 0.49 | 1.11 - | 19.2 | 14.6 | 18.2 | 67.2 |
| 23 | 133 | 415 | 500 | 75 | 500 | 0.50 | 1.66 | 12.9 | 15.1 | 17.1 | 67.8 |
| 24 | 84/$N_2$ | 390 | 508 | 53 | 397 | 0.82 | 1.83 | 12.3 | 12.0 | 16.0 | 72.0 |
| — | 130 | 420 | 530 | 89 | 506 | 0.41 | 0.97 | 20.2 | 15.7 | 12.2 | 72.1 |
| 25 | 134 | 404 | 490 | 91 | 519 | 0.43 | 1.17 | 19.3 | 16.2 | 12.9 | 70.9 |
| 26 | 135 | 393 | 489 | 91 | 555 | 0.41 | 1.15 | 19.5 | 15.9 | 15.6 | 68.5 |
| 27 | 137 | 418 | 488 | 84 | 550 | 0.42 | 1.17 | 19.1 | 16.1 | 18.5 | 65.4 |
| 28 | 138 | 394 | 488 | 93 | 550 | 0.44 | 1.17 | 17.5 | 15.7 | NA | NA |
| 29 | 139 | 404 | 489 | 80 | 550 | 0.44 | 1.16 | 17.7 | 16.1 | NA | NA |
| 30 | 140/$N_2$ | 388 | 475 | 77 | 550 | 0.88 | 1.23 | 13.3 | 13.3 | 11.2 | 75.0 |

*Oil by difference, includes water of pyrolysis

TABLE V

SUMMARY OF NEUTRALIZATION AND EXTRACTION CONDITIONS
Values Given are Net per kg Dry Wood Fed in the Pyrolysis Run

| P/N No. | RUN | DRY WOOD[9] FED kg | Net Condensates* kg | BASE[8] kg | WASH EA, kg | TOTAL EA, kg | P/N | SOLID PPT, kg | BASE[8] gew | FINAL pH |
|---|---|---|---|---|---|---|---|---|---|---|
| 1 | 110 | RW 19.4 | 0.54[6] | — | 0.038 | ? | 0.15 | — | — | |
| 2 | 82 | CP 24.7 | 0.63[6] | — | — | ? | 0.15 | — | — | |
| 3 | 101 | CP 23.6 | 0.55[6] | 0.049 BCS | — | 1.52 | 0.08[5] | — | 0.58 | |
| 3 | 102 | CP 14.5 | 0.66[6] | 0.096 BCS | — | 1.90 | 0.10[7] | — | 1.14 | |
| 4 | 108 | CP 32.3[1] | 1.99 | excess DBC | 0.383 | 2.55 | 0.17 | — | — | 8.0 |
| 5 | 109 | CP 24.7 | 2.47 | 0.089 DBC | 0.244 | 2.56 | 0.18 | — | 1.06[10] | 7.4 |
| 6 | 113 + 114 | CP 56.5 | 2.58 | 0.082 DBC | 0.208 | 2.54 | 0.21 | 0.019 | 0.98[10] | 6.8 |
| 7-8-9 | 116 | CP 26.9 | 2.57 | 0.059 DC | 0.479 | 2.97 | 0.20 | 0.026 | 0.95 | 6.8 |
| 10 | 118 + 119 | CP 65.3[1] | 2.08 | 0.054 DC | 0.483 | 1.60 | | | 0.87 | 7.4 |
| 13-19 | 121[1] | SPI 25.8[1][3] | 1.89 | 0.042 DC | 0.717 | 1.77 | 0.19 | 0.0008 | 0.68 | 6.9 |
| 13-19 | 122 | SPI 78.4 | 1.96 | 0.050 DC | 0.427 | 2.34 | 0.19 | 0.069 | 0.81 | 6.8 |
| 13-19 | 123 | SPI 30.9 | 2.63 | 0.055 DC | 0.510 | 2.39 | 0.19 | 0.031 | 0.89 | 7.3 |
| 13-19 | 124 | SPI 32.4 | 2.38 | 0.054 DC | 1.106 | 3.05 | 0.19 | 0.024 | 0.87 | 6.4 |
| 13-19 | 125 | SPI 116.8 | 2.11 | 0.053 DC | 0.562 | 1.82 | 0.19 | 0.050 | 0.86 | 6.9/6.5 |
| 13-19 | 126 | SPI 124.8 | 2.07 | 0.046 DC | 0.804 | 2.55 | 0.19 | 0.045 | 0.74 | 6.8/7.4 |
| 13-19 | 127 | SPI 119.8[3] | 2.02 | 0.057 DC | 0.860 | 2.45 | 0.19 | 0.044 | 0.92 | 7.4 |
| 20 | 130 | SPI 59.4 | 2.17 | 0.082 DC | 1.102 | 2.90 | 0.14 | 0.0032 | 1.32 | 7.15 |
| 21 | 131 | SP2 43.7 | 1.94 | 0.074 DC | 0.699 | 2.34 | 0.18 | 0.046 | 1.19 | 7.4 |
| 22 | 132 | SP3 32.3 | 1.97 | 0.076 DC | 0.789 | 2.62 | 0.18 | 0.028 | 1.23 | 7.5 |
| 23 | 133 | SPIM 39.5[4] | 2.61 | 0.090 DC | 0.939 | 3.29 | 0.16 | 0.039 | 1.45 | 7.8 |
| 24 | 84 | A 18.3 | 0.61 | — | — | — | ? | — | — | |
| 25 | 134 | SPI 37 | 1.29 | 0.046 DC | 0.11 | 0.41 | 0.13 | 0.00004 | 0.74 | 6.9 |
| 26 | 135 | SPI 55 | 1.84 | 0.042 DC | 0.13 | 0.46 | 0.19 | 0.0010 | 0.68 | 6.9 |
| 27 | 137-139 | SPI 57 | 1.84 | 0.040 DC | 0.07 | 0.43 | 0.18 | 0.0021 | 0.65 | 6.9 |
| 28 | 137-139 | SPI 124 | 1.84 | 0.057 DC | 0.07 | 0.43 | 0.18 | 0.0032 | 0.96 | 7.7 |
| 29 | 137-139 | SPI 121 | 1.84 | — | 0.07 | 0.43 | 0.24 | 0.00008 | 0 | 2.3 |
| 30 | 140 | Oak 24.3 | 0.74 | 0.048 DC | 0.13 | 0.15 | 0.14 | 0.00002 | 0.77 | 6.9 |
| 31 | Waterloo | SPI 9.0 | — | 0.043 DC | — | 0.35 | 0.19[10] | 0.00016 | 0.81 | 6.8 |
| 32 | Red Arrow I | Maple ~60 | 0.7 | 0.051 DC | — | 0.34 | 0.27 | 0.00041 | 0.83 | 6.8 |
| 33 | Red Arrow II | Maple ~32 | 0.7 | 0.053 DC | — | 0.19 | 0.19 | 0.0003 | 0.86 | 6.9 |

*Aqueous and Organic Condensate (no ethyl acetate)
[1] Corrected for slip stream removed for catalyst bed
[2] Extra water added
[3] Condensate samples removed, feed amount adjusted accordingly
[4] Bone dry basis, but 8% moisture in feed
[5] Oils washed excessively during extraction
[6] N₂ carrier gas
[7] neutralization problems
[8] 5% sodium bicarbonate solution (BCS), dry sodium bicarbonate (DBC), dry sodium carbonate monohydrate (DC)
[9] Colorado Pibne (CP); Southern Pine-South Boston, VA (SPI); Southern Pine-Montecello, GAS (SP2); Southern Pine-Russelville, SC (SP3)
[10] PN Yields based on oil condensate delivered and assumes 70% conversion from dry wood.

TABLE VI

Comparison of Pyrolysis/Neutralization Conditions with Gel times and resole viscosities for 25% and 50% phenol replacement with PN product

| Run # | PN # | pH | T crack C | time crack msec | Exit Pyr C | Approx. Severity Thermal | Severity -pH | 50% PN Gel time sec | Resole Viscosity cps | 25% PN Gel time sec | Resole Viscosity cps |
|---|---|---|---|---|---|---|---|---|---|---|---|
| 121-127 | XX-84 MB | 6.9 | 441 | 514 | 495 | 38.9 | 32.0 | 93.5 | 880 | 78.5 | 630 |
| 121-127 | Aristech | 6.9 | 441 | 514 | 495 | 38.9 | 32.0 | 70.0 | 1070 | 82.0 | 630 |
| 130 | 619-108 | 7.2 | 506 | 410 | 530 | 44.6 | 37.4 | 117.5[a] | 1070 | 85.5 | 630 |
| 131 | XXI-71 | 7.4 | 497 | 490 | 520 | 43.7 | 36.3 | 63.5 | 1290 | 97.0 | 690 |
| 132 | XXI-67 | 7.5 | 492 | 490 | 490 | 41.5 | 34.0 | 90.3 | 880 | 114.5 | 590 |
| 133 | XXI-79 | 7.8 | 500 | 500 | 500 | 42.6 | 34.8 | 78.0 | 880 | 85.0 | 590 |
| 134 | 723-48 | 6.9 | 519 | 430 | 490 | 43.0 | 35.1 | 88.5 | 880 | 87.0 | 690 |
| 135 | 723-44 | 6.9 | 555 | 410 | 489 | 45.0 | 38.1 | 73.5 | 1070 | 56.5 | 880 |
| 137-139 | 723-51 | 6.9 | 550 | 420 | 488 | 44.6 | 37.7 | 72.5 | 1070 | 100.5 | 550 |
| 137-139 | 723-55 | 7.7 | 550 | 440 | 488 | 44.7 | 37.0 | 74.0[b] | 1070 | 92.5 | 590 |
| 137-139 | 723-58 | 2.5 | 550 | 440 | 489 | 44.7 | 42.2 | 71.0[c] | 1290 | 77.0 | 630 |
| 140 | 723-63 | 6.9 | 550 | 880 | 475 | 44.6 | 37.7 | 63.0 | 1070 | 85.5 | 590 |
| 141 | 723-45 | 6.8 | Waterloo | | | | | 79.5 | 880 | 104.5 | 590 |
| 142 | 723-46 | 6.8 | RedArrow I | | | | | 65.5 | 1760 | 90.5 | 750 |
| 143 | 723-64 | 6.9 | RedArrow II | | | | | 84.5 | 1290 | 77.5 | 630 |
| Phenol-1 | | NA | NA | NA | NA | | | 112.5 | 550 | | |
| Phenol-2 | | NA | NA | NA | NA | | | | | 80.0 | 470 |

[1] first addition of 10 g NaOH followed by a second addition of the same amount of base
[2] first addition of 20 g of NaOH followed by a second addition of 10 g NaOH Note:
All phenol/PN products resoles were made with 20 g NaOH first followed by 10 g NaOH
[a] Repeat of this cook produced a resole of 600-1000 cps viscosity and 118-124 sec gel time (average 122) at 120° C.
[b] Repeat of this cook was taken to various cuts in viscosity: 1070, 9850, and 20,000 cps, respectively, product gel times at 120° C. of 102, 77, and 79 seconds.
[c] Repeat of this cook produced a resole of 450 cps viscosity and 132-140 sec gel time (average 136 sec).

Table VI presents a comparison of pyrolysis/neutralization conditions with gel times and resole viscosities for 25% and 50% phenol replacement with PN product. Note that several repetitions of the preparations have been made, with viscosities that vary within acceptable ranges for plywood manufacture as well as for other resole applications such as a variety of composite boards and paper overlays.

The P/N products from the oils of Samples #31, 32 and 33 are compared with those from similar materials, in which the thermal severity of the treatment varied and the properties of these materials are assembled in Table III, whereas the conditions of extraction are detailed in Table V.

These comparisons were investigated in order to ascertain:

A) whether other oils from different fast pyrolyzer reactors were suitable to produce P/N products for resole formation;

B) whether gel times and resin properties depend on species—both within the Southern pine family and outside; and C) whether gel times/resin properties correlate with the method of production of P/N products, i.e., fractionation conditions.

To obtain answers to question B) above, pines from South Boston, Monticello and Russelville were investigated in order to observe the characteristics of products from these sources compared to feedstocks of Colorado pines and Douglas Fir bark. Examples of other species are Oak and Maple.

In order to assess the resole formation with resins that would permit assessment of differences between fractionation methods, resins were prepared at two levels of phenol substitution; i.e., 25% and 50% by weight.

PROCEDURE

Base was added in two stages, with a large excess in the first addition, in which base and formaldehyde were added, and a second addition of less sodium hydroxide. The final viscosity was controlled in cooking each resin, so that the resulting resin would be in a range deemed feasible for a plywood resin as well as composite boards (particle board, oriented board, and strand board) and paper overlays. Table VI shows the resole viscosities and gel times at 120° C.

An illustration is: to 29.1 g P/N (equivalent to 25%)+70 g of phenol, 20 g NaOH (50% wt) and 143 g of formaldehyde (37%) were added—temperature and viscosity were followed as a function of time; a second addition of half of the initial amount of NaOH is added while the viscosity is controlled. For the example with the resin from run 132, the final viscosity achieved was TU (590 cps) and the gel time at 120° C. was 112 seconds for the first measurement and 117 seconds for the second one. Resin reproducibility was good for gel times and less accurate for viscosity which could vary widely with cooking conditions as shown in three examples of Table VI; cooking conditions are key to achieving the desirable viscosity and gel times. The corresponding resin at 50% substitution gave gel times of 88 and 92 seconds and a viscosity of 880 cps. Phenol gel times and viscosities under the same conditions that the substituted resins were prepared were 79 and 81 seconds and 470 cps. Using half of the amount of base added in the first step and a similar amount in the second step, these numbers increase to 115 and 110 seconds and 550 cps. While these latter conditions are more normal for plywood resin preparation, it should be kept in mind that the goal is to demonstrate differences between fractionated materials and not necessarily to optimize each preparation. The viscosities demonstrated in these preparations would be suitable for a variety of applications ranging from plywood to various composite boards and paper overlays.

In order to ascertain whether the P/N materials reacted with formaldehyde and/or phenol, representative resoles were taken to partial cure, such that the extraction of the not fully reacted materials could be observed and the extracts characterized. These extracts were compared to the pure phenol resins. From a 3-minute cure in a hot plate (3 g sample), the materials were ground up and solubilized sequentially in water and tetrahydrofuran. One gram of the partially cured resole was extracted overnight with 30.0 mL of water (shaker table) at room temperature; the aqueous solution was separated and freeze dried for extractives determination. The residue was dried overnight and resuspended in THF for further assessment of solubilization of intermediates (30 mL/g).

The phenol resoles produced roughly 8% of extractable organic materials. FTIR spectrum of the extract had main absorption peaks at (absorption given in parenthesis) 765 (0.13), 802 (0.08), 831 (0.09), 1017 (0.14), 1300 (0.35), 1354 (0.36), 1446 (1.16), 1603 (0.6), and 1697 (0.1)cm$^{-1}$. These absorption peaks are characteristic of oligomeric phenolic structures bonded by $CH_2$ groups, having methylol groups.

The amount of extractives under similar conditions of partial cure of the P/N-phenol (50%) resoles varied from 16.8% (oak, high severity sample) to 23% for three samples of intermediate severity samples of southern pine to 30-60% for the low severity Southern pine sample. The FTIR spectra of these extracts did not resemble those of the original P/N products, but produced the following key spectral features: peak position in cm$^{-1}$ (absorbance) 766 (0.26); 0.773 (0.28), 881 (0.09), 1044 (0.33), 1298 (0.295), 1355 (1.26), 1368 (1.1), 1413 (0.74), 1448 (0.94), 1629 (2.2). These characteristics are very dissimilar to the original P/N material and are significantly increased in the resole in the 760-880 cm$^{-1}$ range, characteristic of methylene groups; the dominant peak at 1629 cm$^{-1}$ is characteristic of multiply substituted phenyl rings, and the disappearance of the 1512 cm$^{-1}$, which characterizes the neat P/N products due to the aromatic skeletal ring vibrations typical of aromatic structures with at least three ring hydrogen atoms and increase in the 1629 cm$^{-1}$ peak, indicating multiple substitution. The fingerprint region 1000-1400 cm$^{-1}$ of the P/N product has also changed appearance drastically, suggesting that the P/N product has reacted with phenol/formaldehyde to produce oligomers that contain methylol groups and methylene-bonded phenyl compounds. Very little unreacted material can be detected by FTIR. The P/N materials reacted and produced oligomers/polymers. Reaction conditions in the preparation of the P/N products influence the extent of reaction, thus providing a tool for reactivity assessment of the P/N products.

RESULTS AND INTERPRETATION

Important parameters in thermal severity are:

1) pyrolysis reactor temperature and vapor residence time (including vapor residence time in the reactor and recycle loop, as it is a very difficult parameter to calculate and the temperature is assumed constant, although there were small variations from experiment to experiment);

2) temperature and residence time in the vapor cracker (these were measured experimentally—an average vapor cracker temperature was used here); and 3) sequence of condensation temperatures (less severe than the above ones and assumed constant).

Thermal Severity

Effects of time and temperature can be jointly observed to provide a guide for the production of the P/N product as far as acceptable time/temperature profiles are concerned. This treatment is based on severity concepts in the literature that have been utilized in pulping, fractionation of lignocellulosics, and other processes [e.g., K. E. Vroom, "The "H" factor: A means of expressing cooking times and temperatures as a single variable", Pulp and Paper Magazine of Canada, vol. 58, pp. 228-231 (1965); R. P. Overend and E. Chornet, "Fractionation of Lignocellulosics by Steam-aqueous pretreatment", Phil. Transaction of the Royal Society London, A, vol. 321, pp. 523-536, 1987].

A reaction ordinate, the severity factor, is defined as $R_w = \exp[(T_r - T_b)/w] * t$, where $T_r$ is the reaction temperature, $T_b$ is the base temperature (a temperature at which the reactions are negligible), t is the duration of the reaction, and w is an experimental parameter, related to the activation energy, and equal to 16 or 17 degrees K in the present case (26 kcal/mol and 29.8 kcal/mol, respectively for pyrolysis and vapor thermal cracking). The severity results are approximate, while the thermal cracking results are experimental and more reliable than those estimated for the pyrolysis step alone. The base temperature was chosen at 200° C. Table VI shows the results of these calculations for several Southern pines and for oak.

Thermal severity-pH

The effect of the neutralization was added by including the pH at which that operation was carried out. The treatment followed literature references: H. L. Chum, D. K. Johnson, and S. K. Black, "Organosolv Pretreatment for Enzymatic Hydrolysis of Poplars. II. Catalyst Effects and the Combined Severity Parameter," *Ind. Eng. Chem. Res.* Vol. 29, 156-162, 1990; H. L. Chum, S. K. Black, D. K. Johnson, and R. P. Overend, "Pretreatment-Catalyst Effects and the Combined Severity Parameter" *Appl. Biochem. Biotechnol.* Vol. 24/25, pp. 1-14, 1990. This combined severity parameter is also shown in Table VI.

The two initial points in the table are approximate since the severity was calculated as an average of pyrolysis conditions from runs 121-127, and therefore, these numbers should be considered approximate. The actual parameters are better known in runs 131-140.

By using factor analyses of the FTIR results, the thermal severity, and the pH, a good correlation can be observed between the spectral properties and these variables, which is illustrated in FIG. 8A.

The correlation includes factors 3 and 4, which contain wave numbers of 1711 and 1263 cm$^{-1}$. These wavenumbers are associated with C=O stretches in conjugated C=C systems and C—O—CH$_3$ in the P/N products. Those frequencies are chemically quite sensible for correlations since the higher the amount of methoxyl groups left, the slower the reactivity; the higher the C=O, C=C systems content, the higher the reactivity. The correlation observed involves spectral factors*severity—4*spectral factors*pH, and produces a correlation coefficient around 0.6.

Therefore, thermal cracking severity—pH are representative of the overall severity of the production of P/N materials, and this ordinate is used in Table VI.

ANALYSES OF GEL TIMES/VISCOSITY AS A FUNCTION OF THERMAL SEVERITY AND THE COMBINED THERMAL SEVERITY/PH

Figure 8B:
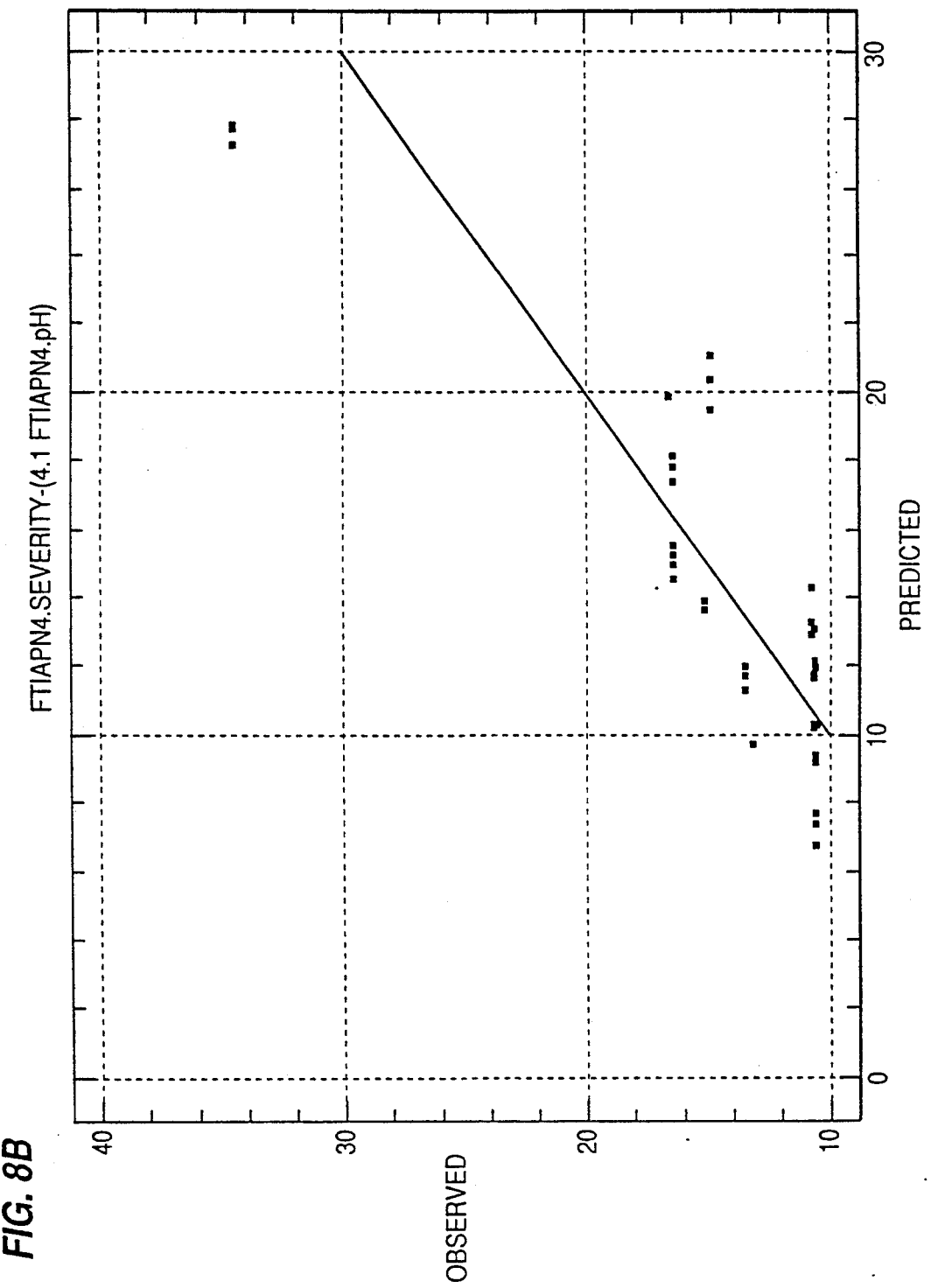
FIG. 8B is a graph of the thermal severity permitting grouping of the relative severity of various samples from a thermal point of view, where the numbers indicate the run employed and may be cross-checked with conditions in Table VI and III-V.

The thermal severity permits grouping of the relative severity of the preparation of these various samples from a thermal point of view only (see FIG. 8B). The numbers used indicate the run employed and can be cross-checked with conditions in Tables VI and III-V:

High Severity Group (44-45) 135 (45)≈137-139 (44.7)≈130 (44.6)=140 (oak, 44.6)

Intermediate Severity Group (41-44) 131 (Monticello, 43.7)≧134 (43)≈133 (Wet South Boston, 42.6)

Low Severity Group (<42) 132 (Russelville, 41.5)>121-127 (39, poor calculation since it is averaging seven runs—the number has at least a ±4 error); this group of samples could easily be in a higher severity group.

With the exception of samples from run 130, and the two from low severity runs, 121-127 and 132, all materials make resoles of gel times from 60-80 seconds, which are equal to or smaller than that for phenol, as displayed in FIG. 8B or Table VI. The gel times (where the first number represents 50% substitution, and the second number represents 25% substitution) are as follows:

High Severity Group (at constant pH 7±0.1) 135 (73.5, 56.5)<137-139 (72.5, 100.5)≈130 (117.5, 85.5)>140, oak (63, 85.5)

Intermediate Severity Group (pH of samples varied—average 7.4±0.4) 131 pH 7.4 (63.5, 97)≦134 pH 6.9 (88.5, 87)≈133 pH 7.8 (78, 85)

This group of samples of similar thermal severity illustrates the very good reproducibility obtained from different Southern pines, including one sample (133) which was at 7% moisture content versus dried feed. Samples from Monticello, South Boston dry, and South Boston wet were obtained under similar reactor conditions and calculate to be in the same thermal severity group. The differences in pH appear to be responsible for some of the trends seen. The average gel time at 50% substitution is 77±12 and at 25% substitution is 89±6. Both of these values are within two standard deviations from the mean gel time of 80 seconds for phenol alone. Standard deviation for single measurements is ±3 seconds.

Low Severity Group 132 pH 7.5 (90.3, 114.5); 121-7 pH 6.9 (93.5, 78.5; 70, 82)

It should be noted that the Russelville sample, which had a significantly lower thermal severity gave a resole with gel times that were significantly higher than the previous samples. This fact suggests that severity parameters can be used for operational control of pyrolysis/thermal cracking.

All resoles at 50% substitution have gel times that were smaller than or equal to 80 seconds (with the exception of three samples from runs 130, 132, and 121-127 (Master Batch) which gave gel times of 117.5, 93.5, and 90.3, respectively). The outliers tend to be in the low severity area. The Aristech P/N sample had a higher severity than the corresponding Master Batch because of a higher temperature-time profile during solvent evaporation, which lends support to the idea that the higher severity samples appear to give equal or smaller gel times than phenol alone.

The thermal severity correlations parallel the extractives removed from the partially cured resoles: run 140 (oak), severity 44.6, 16.8% extractives runs 137-9 at pH 2.3 or 6.9, severity 44.6, 23.5% extractives run 133, severity 42.6, 24% extractives run 121-127, XX-84 MB, severity 38.9, 28% extractives run 121-127, Aristech samples, severity 38.9, 68% extractives. In general terms, the higher the severity of the thermal process, the lower the amount of extractives removed from the partially cured resole.

At 25% substitution, only the P/N produced at the highest thermal severity has a gel time significantly smaller than 80 seconds (56 seconds). Next, identical within 5 seconds, are the samples with high severity (oak, 85.5 seconds, runs 130, 133, and 137-139 at the highest severity, with 77 seconds). Higher than 85 seconds are samples: 130, 131, 134, 137-9 at pH 6.9 and 7.7, and Waterloo, three of which have intermediate severity.

Ten P/N substituted samples gave higher resole gel time at 25% substitution than at 50%, while four were lower, and appears to indicate a higher reactivity between P/N species than P/N-phenol species reacted with formaldehyde or with their own reactive groups.

When the pH is included into the severity parameter estimation, the following are the groupings:

High Severity Group (42) 137-9 pH 2.5 (42)
Intermediate Severity Group (35-38) 135 (38.1)≧137-9 pH 6.9 (37.7)=140 (oak, 37.7)≈130 (37.4)≈137-9 pH 7.7 (37)≧131 (Monticello, 36.3)≈134 (36.1)≧133 (Wet South Boston, 34.1)
Low Severity Group (<35) 132 (Russelville, 34)>121-127 (poor calculation since it is averaging seven runs—the number 32 can have at least a ±4 error); these two samples may easily be in a higher severity group.

With exception of the sample from run 130, the groupings lead to materials of very similar gel times, as displayed in Table VI. The gel times (first number 50%, second number 25% substitution levels) are as follows:

High Severity Group 137-9 pH 2.5 (71, 77)
Intermediate Severity Group 135 (73.5, 56.5)<137-139 pH 6.9 (72.5, 100.5)<140 (63, 85.5)<130 (117.5, 85.5)>137-9 pH 7.7 (74, 92.5)>131 (63.5, 97)≦134 (88.5, 87)≦133 (78, 85)
Low Severity Group 132 (90.3, 114.5); 121-7 (93.5, 78.5; 70, 82)

From these comparisons, it appears that: pH enables one to see more differences between samples than would have been seen when applying the thermal severity test alone (except for extractables content), and that the samples with variable pH follow a trend, although both the thermal severity calculations and the pH determinations in non-aqueous/aqueous media offer substantial experimental errors: 137-9 pH 2.5 (71, 77)<137-139 pH 6.9 (72.5, 100.5)≈137-9 ph 7.7 (74, 92.5)

These results suggest that the dominant factor is the thermal severity, but pH control allows an additional degree of control of the suitability of the material for replacement of phenol in phenol/formaldehyde resins.

The viscosity of the resoles can be also grouped in an analogous manner. However, the resole advancement and its viscosity can be controlled during cooking.

From the foregoing data, it can be seen that many of the samples prepared can replace 25% or 50% of phenol in resoles.

It is possible to guide the conditions of P/N product preparation such that the P/N-containing resoles have acceptable gel times and viscosities. The pH should be near 6.9±0.5, although a wider range of pH can be used between 2.3-7.7. The impact of the use of a pH 2.3 material is that more water leachable material can be incorporated into the resin, however, there are no detectable differences in partially cured resoles extractables from these samples prepared at pH 2.3 or 6.9, within the experimental error. However, the higher pH is not desirable because it tends to form more precipitate in the neutralization/extraction steps (see Table IV).

The maple samples at 50% replacement have lower gel times than phenol. These samples gave higher viscosity resoles; however, since these runs are with maple, it is more difficult to assess the viscosity/gel time relationship with the unknown thermal treatment conditions. The second sample has a more acceptable gel time at 25% substitution, and the decrease in resole viscosity is parallel to that observed in the other samples.

The oak sample is a good example of a high severity P/N product that can be employed with acceptable properties at 25% and significantly better gel times at 50% relative to phenol.

A wide range of P/N products has been prepared that is suitable for replacement of phenol in resole resins. The inherent reactivity of the material is used to best advantage by substituting 50% of phenol by the P/N material versus the lower level of substitution. Intermediate to high severity conditions are best for the production of faster curing materials at 50% substitution. The trend appearing from the data is that by increasing the severity further, the viscosity of the resulting resole may be affected.

What is claimed is:

1. An improved process for preparing phenol-formaldehyde resole resins by fractionating organic and aqueous condensates made by fast-pyrolysis of biomass materials while using a carrier gas to move feed into a reactor to produce phenolic-containing/neutrals suitable for manufacturing phenol-formaldehyde resole resins, said process comprising:

admixing said organic and aqueous condensates with basic materials selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, hydrates thereof, or mixtures thereof to neutralize acidic components of the condensates and to render said acidic components and polar compounds less soluble in organic phase;

admixing said neutralized condensates with an organic solvent having approximately 8.4 to 9.1 $(cal/cm^3)^{\frac{1}{2}}$ with polar components in the 1.9-3.0 range, a solubility parameter and hydrogen bonding components in the 2-4.8 range to extract phenolic-containing and neutral fractions from the organic and aqueous phases into a solvent phase;

separating the organic solvent-soluble fraction having the phenolic-containing and neutrals fractions from the aqueous fraction;

removing the organic solvent to produce said phenolic-containing and neutrals compositions in a form substantially free from said solvent; and substituting said phenolic-containing and neutrals composition for a portion of phenol in a phenol-formaldehyde resole composition.

2. A process for fractionating organic and aqueous condensates made by fast-pyrolysis of biomass materials while using a carrier gas to move feed into a reactor to produce phenolic-containing/neutrals extract, wherein the neutral fractions have molecular weights of 100 to 800; said extract being suitable for a part of phenol for manufacturing phenol-formaldehyde resole resins, said process comprising:
   admixing said condensates with an organic solvent having a solubility parameter of 8.4 to 9.1 $(cal/cm^3)^{\frac{1}{2}}$ with polar components in the 1.9–3.0 range and hydrogen bonding components in the 2–4.8 range to extract phenolic-containing and neutral fractions from said condensates into a solvent phase;
   admixing said organic and aqueous condensates with basic materials selected from the group consisting of sodium hydroxide, sodium carbonate, sodium sesquicarbonate, potassium hydroxide, potassium carbonate, ammonium hydroxide, ammonium carbonate, lithium hydroxide, lithium carbonate, calcium hydroxide, calcium carbonate, magnesium hydroxide, magnesium carbonate, hydrates thereof, or mixtures thereof to neutralize acidic components of the condensates and to render said acidic components and polar compounds less soluble in organic phase;
   separating the organic solvent-soluble fraction having the phenolic-containing and neutral fractions from the aqueous fraction; and
   removing the organic solvent to produce said phenolic-containing and neutrals compositions in a form substantially free from said solvent; and
   substituting said phenolic-containing and neutrals compositions for a portion of phenol in phenol-formaldehyde resole composition.

3. The process of claim 1, wherein said organic solvent is selected from the group consisting of ethyl acetate, butyl acetate, methylisobutyl ketone and mixtures thereof.

4. The process of claim 2, wherein said organic solvent comprises ethyl acetate.

5. The process of claim 4, wherein the extraction utilizing ethyl acetate solvent is performed at a pH of approximately 6 to 8.

6. The process of claim 5, wherein the extraction utilizing ethyl acetate solvent is performed at a pH of about 6.5 to 7.5.

7. The process of claim 1, wherein said basic material is in a dry, solid state.

8. The process of claim 1, wherein said basic material is dry sodium bicarbonate.

9. The process of claim 1, wherein said basic material is dry sodium carbonate.

10. The process of claim 1, wherein said basic material is a dry, hydrated form of sodium carbonate.

11. The process of claim 1, wherein said basic material is dry calcium carbonate.

12. The process of claim 1, wherein said basic material is dry calcium hydroxide.

13. The process of claim 1, wherein said basic material is an aqueous solution of sodium carbonate.

14. The process of claim 1, wherein said basic material is a slurry of sodium bicarbonate.

15. The process of claim 1, wherein said basic material is a slurry of sodium carbonate.

16. The process as claimed in claim 1, wherein said basic material is a slurry of calcium carbonate.

17. The process of claim 1, wherein said basic material is a slurry of calcium hydroxide in a suitable liquid.

18. The process of claim 1, wherein said neutralized pyrolysis condensates and condensed carrier steam are admixed with said organic solvent in a solvent-to-dry-pyrolyzed-feed ratio of between 1 to 5 by weight, including solvent used to wash condensing equipment and/or to transfer the condensates into a neutralization tank.

19. The process of claim 1, wherein said organic solvent is removed from a residual organic fraction by evaporation to provide a substantially solvent free phenolic-containing/neutrals composition.

20. The process of claim 1, wherein said fast-pyrolysis condensates are produced from biomass materials that are lignocellulosic materials.

21. The process of claim 20, wherein said lignocellulosic materials are selected from the group consisting of softwoods, hardwoods, bark of tree species, and grasses.

22. The process of claim 20, wherein said softwoods are selected from pine and redwood.

23. The process of claim 20, wherein said hardwood is aspen, oak or maple.

24. The process of claim 20, wherein said bark of tree species is Douglas fir.

25. The process of claim 20, wherein said grass is bagasse.

26. The process of claim 1, wherein said phenolic-containing/neutrals fraction compositions are capable of substituting from 5% to 75% of phenol in phenol-formaldehyde resins.

27. The process of claim 18, wherein said phenolic-containing/neutrals compositions include a high phenolic, hydroxyl and aldehyde content.

28. The process of claim 18, wherein said organic solvent is evaporated from a residual organic solvent fraction, and said phenolic-containing/neutral composition is in a substantially solvent free condition to form a basis for resin applications, such as molding compounds and wood adhesives for plywood, particle board, strand board, fiberboard, and paper overlay applications.

29. The process of claim 1, wherein said process is a series of batch processes.

30. The process of claim 1, wherein said process is a series of continuous processes.

31. The process claim 1, wherein said process is a mixture of batch and continuous processes.

32. The process of claim 30, wherein said neutralization is a batch process and the extraction is a continuous process.

33. A resole resin containing the phenolic-containing and neutral fraction produced by the process of claim 1.

34. The process of claim 2, wherein the carrier gas is noncondensible recycled gas.

35. The process of claim 2, wherein said basic material is in a dry state and is selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, or hydrates thereof, or mixtures thereof.

36. The process of claim 35, wherein said basic material is in a dry state is sodium bicarbonate.

37. The process as claimed in claim 35, wherein said basic material is in a relatively dry state and is sodium carbonate or hydrates of sodium carbonate.

38. The process as claimed in claim 35, wherein said basic material in a dry state is sodium sesquicarbonate.

39. The process as claimed in claim 35, wherein said basic material in a dry state is calcium carbonate.

40. The process as claimed in claim 35, wherein said basic material in a dry state is calcium hydroxide.

41. The basic material of claim 2, wherein said basic material is in a slurry form in a suitable liquid.

42. The process of claim 2, wherein said neutralized pyrolysis condensates and condensed carrier steam are admixed with ethyl acetate solvent in a solvent-to-dry lignocellulosic-feed ratio of between 1 to 5 by weight, including solvent used to wash condensing equipment and/or to transfer the condensates into a neutralization tank.

43. The process of claim 42, wherein said ethyl acetate is removed from a residual organic fraction by evaporation to provide a substantially solvent free phenolic-containing/neutrals composition.

44. The process of claim 42, wherein said lignocellulosic materials are selected from the group consisting of : softwoods, hardwoods, bark, and grasses.

45. The process of claim 44, wherein said softwoods are pine and redwood.

46. The process of claim 44, wherein said hardwood is aspen, oak and maple.

47. The process of claim 2, wherein said phenolic-containing/neutrals fraction compositions are capable of substituting for up to 75% of phenol in phenol-formaldehyde resole resins.

48. The process of claim 39, wherein said phenolic-containing/neutrals compositions include a high phenolic hydroxyl and aldehyde content.

49. The process of claim 42, wherein said ethyl acetate solvent is evaporated from a residual organic fraction, and said phenolic-containing/neutral composition is in a substantially solvent free condition to form a basis for molding compounds and adhesives for wood bonding such as plywood, composite board, oriented board, particles board, and paper overlays.

50. The process of claim 2, wherein a portion of said organic solvent/pyrolysis condensate not extracted into an organic solvent-soluble fraction is further processed utilizing zeolite catalysts to form gasoline.

51. The process of claim 2, wherein said process is a series of batch processes.

52. The process of claim 2, wherein said process is a series of continuous processes.

53. The process of claim 2, wherein said process is a mixture of batch and continuous processes.

54. The process of claim 2, wherein said neutralization is a bath process and said extraction is a continuous process.

55. An adhesive resin having the phenolic-containing and neutrals fraction produced by the process of claim 35.

56. A process for fractionating organic and aqueous condensates made by fast-pyrolysis of lignocellulosic materials while using steam as a carrier gas to move feed into and char out of a reactor to produce a phenolic-containing/neutral composition suitable for manufacturing phenol-formaldehyde resole resins, said process comprising:

admixing said organic and aqueous condensates with dry sodium carbonate to neutralize acidic components of the condensates to a pH of between about 6.5 and 7.5 to render such acidic components and other polar compounds less soluble in an organic phase;

admixing said neutralized condensates with ethyl acetate in a weight ratio of ethyl acetate solvent to dry lignocellulosic feed of between 1 to 5 kg of ethyl acetate per kg of feed to extract phenolic-containing and neutral fractions from organic and aqueous phases into an ethyl acetate phase;

separating an ethyl-acetate-soluble fraction having the phenolic-containing and neutral fractions from the aqueous fraction;

removing the ethyl acetate solvent to produce said phenolic-containing and neutrals compositions in a form substantially free from ethyl acetate; and substituting said phenolic-containing and neutrals compositions for a portion of phenol in a phenol-formaldehyde resole composition.

57. An article selected from plywood, particle board, strand board, fiber board and paper overlay containing the phenolic-containing and neutrals fractions product of claim 61.

58. The process of claim 1, wherein the carrier gas is noncondensible recycled gases in which sufficient water is present in the condensates of fast-pyrolysis to form an aqueous phase and an organic phase, and wherein said aqueous phase is sufficiently large to extract water soluble organic compounds from the organic phase and to serve as an ionizing media for material used to neutralize acidic organic compounds present.

59. The process of claim 2, wherein the carrier gas is noncondensible but contains sufficient water in the condensates of fast-pyrolysis to form an aqueous phase and an organic phase, and wherein said aqueous phase is sufficiently large to extract water soluble organic compounds from the ethyl acetate phase and to serve as ionizing media for material used to neutralize acidic organic compounds present.

60. The process of claim 17, wherein said organic solvent is evaporated in a way to produce a product having sufficient water remaining to provide a lower viscosity for ease of handling.

61. The process of claim 42, wherein said organic solvent is evaporated in a way to produce a product having sufficient water remaining to provide a lower viscosity for ease of handling.

62. The process of claim 56, wherein said ethyl acetate is removed by evaporation in a way to produce a product having sufficient water remaining to provide a lower a viscosity for ease of handling.

63. The process of claim 57, wherein said ethyl acetate is removed by evaporation in a way to produce a product having sufficient water remaining to provide a lower viscosity for ease of handling.

64. The process of claim 60, wherein said organic solvent is partially or wholly evaporated by direct contact with steam.

65. The process of claim 61, wherein said organic solvent is partially or wholly evaporated by direct contact with steam.

66. The process of claim 62, wherein said ethyl acetate is partially or wholly evaporated by direct contact with steam 67. The process of claim 63, wherein said ethyl acetate is partially or wholly evaporated by direct contact with steam 68. The process of claim 1, wherein the organic solvent is recovered from the aqueous phase by evaporation.

69. The process of claim 39, wherein the organic solvent is recovered from the aqueous phase by evaporation.

70. The process of claim 56, wherein the ethyl acetate is recovered from the aqueous phase by evaporation.

71. The process of claim 57, wherein the ethyl acetate is recovered from the aqueous phase by evaporation.

72. The process of claim 68, wherein heat for evaporation is supplied by direct contact with steam.

73. The process of claim 69, wherein heat for evaporation is supplied by direct contact with steam.

74. The process of claim 70, wherein heat for evaporation is supplied by direct contact with steam.

75. The process of claim 71, wherein heat for evaporation is supplied by direct contact with steam.

76. The process of claim 1, wherein pyrolysis vapors are subjected to subsequent controlled thermal treatment after their formation to minimize the formation of precipitates during the neutralization and/or extraction steps.

77. The process of claim 34, wherein pyrolysis vapors are subjected to subsequent thermal treatment after their formation to minimize formation of precipitates during the neutralization and/or extraction steps.

78. The process of claim 56, wherein pyrolysis vapors are subjected to subsequent thermal treatment after their formation to minimize formation of precipitates during the neutralization and/or extraction steps.

79. The process of claim 57, wherein pyrolysis vapors are subjected to subsequent thermal treatment after their formation to minimize formation of precipitates during the neutralization and/or extraction steps.

80. The process of claim 1, wherein the aqueous phase is decanted and neutralized separately from the organic phase and admixed with the organic phase to neutralize the organic phase.

81. The process as claimed in claim 29, wherein the aqueous phase is decanted and neutralized separately from the organic phase and admixed with the organic phase to neutralize the organic phase.

82. The process of claim 56, wherein the aqueous phase is decanted and neutralized separately from the organic phase and admixed with the organic phase to neutralize the organic phase.

83. The process of claim 51, wherein the aqueous phase is decanted and neutralized separately from the organic phase and admixed with the organic phase to neutralize the organic phase.

84. The process of claim 5, wherein a part or all of the solvent used in the extraction is added prior to the neutralization.

85. The process of claim 32, wherein a part or all of the ethyl acetate solvent is added prior to neutralization.

86. The process of claim 49, wherein a part or all of the ethyl acetate solvent is added prior to the neutralization.

87. The process of claim 51, wherein a part or all of the ethyl acetate solvent is added prior to neutralization.

88. The process of claim 1, wherein steam recycled gases plus steam and an inert gas is the carrier gas.

89. The process of claim 1, wherein said organic solvent also exhibits low mutual solubility with water.

90. The process of claim 1, wherein said organic solvent is selected from the group consisting of methyl ketone, ethyl ketones and mixtures thereof.

91. The process of claim 2 wherein said biomass materials are lignocellulosic materials selected from the group consisting of softwoods, hardwoods, pine sawdust, bark, grasses and agricultural residues.

92. The process of claim 1 wherein said phenolics/neutral fractions extract replaces 5% to at least 75% by weight of the phenol in said phenol-formaldehyde resole resins.

93. The process of claim 1 wherein said phenolics/neutrals fractions extract replaces 5% to at least 50% by weight of the phenol in said phenol-formaldehyde resole resins.

94. The process of claim 1 wherein said phenolics/neutral fractions extract replaces 5% to at least 25% by weight of the phenol in said phenol-formaldehyde resole resins.

* * * * *